(12) United States Patent
Arepally et al.

(10) Patent No.: US 10,780,250 B1
(45) Date of Patent: Sep. 22, 2020

(54) SYSTEM AND METHOD FOR SELECTIVE PRESSURE-CONTROLLED THERAPEUTIC DELIVERY

(71) Applicant: Surefire Medical, Inc., Westminster, CO (US)

(72) Inventors: Aravind Arepally, Atlanta, GA (US); David Benjamin Jaroch, Arvada, CO (US); Bryan Pinchuk, Denver, CO (US); James E. Chomas, Denver, CO (US)

(73) Assignee: Surefire Medical, Inc., Westminster, CO (US)

( * ) Notice: Subject to any disclaimer, the term of this patent is extended or adjusted under 35 U.S.C. 154(b) by 288 days.

(21) Appl. No.: 15/703,951

(22) Filed: Sep. 13, 2017

Related U.S. Application Data

(60) Provisional application No. 62/396,622, filed on Sep. 19, 2016.

(51) Int. Cl.
*A61M 25/09* (2006.01)
*A61B 17/12* (2006.01)
(Continued)

(52) U.S. Cl.
CPC . *A61M 25/09041* (2013.01); *A61B 17/12022* (2013.01); *A61M 25/0084* (2013.01);
(Continued)

(58) Field of Classification Search
CPC ........ A61M 25/09041; A61M 25/0084; A61M 25/065; A61M 25/1011;
(Continued)

(56) References Cited

U.S. PATENT DOCUMENTS 926,591 A   6/1909 Odquist
4,261,341 A  4/1981 Hakim
(Continued)

FOREIGN PATENT DOCUMENTS

DE   8910603 U1   12/1989
EP   0533511 A1    3/1993
(Continued)

OTHER PUBLICATIONS

US 7,169,126 B2, 01/2007, Zadno-Azizi (withdrawn)
(Continued)

*Primary Examiner* — Brandy S Lee
*Assistant Examiner* — Nidah M Hussain
(74) *Attorney, Agent, or Firm* — Gordon & Jacobson, P.C.

(57) ABSTRACT

A treatment system includes a guide sheath, and a catheter provided with a pressure-controlled element. The pressure-control element preferably includes an expanded configuration adapted to extend across a small feeder vessel branching from the splenic vein. The pressure-control element is positioned with the feeder vessel, and a therapeutic agent is delivered under pressure directly into the feeder vessel, where it is forced to penetrate deep into tissue. Pressure responsive elements for monitoring intravascular pressure are also provided to time delivery of the therapeutic agent for maximum uptake by the target organ.

22 Claims, 10 Drawing Sheets

(51) Int. Cl.
*A61M 25/00* (2006.01)
*A61B 17/34* (2006.01)
*A61M 25/06* (2006.01)
*A61B 17/22* (2006.01)
*A61K 9/00* (2006.01)
*A61M 25/10* (2013.01)

(52) U.S. Cl.
CPC ........... *A61B 17/22* (2013.01); *A61B 17/3423* (2013.01); *A61K 9/0019* (2013.01); *A61M 25/065* (2013.01); *A61M 25/1011* (2013.01); *A61M 2025/0681* (2013.01)

(58) Field of Classification Search
CPC ........... A61M 2025/0681; A61B 17/22; A61B 17/12022; A61B 17/3423; A61K 9/0019
USPC ....................................................... 604/500
See application file for complete search history.

(56) References Cited

U.S. PATENT DOCUMENTS

| | | |
|---|---|---|
| 4,311,587 A | 1/1982 | Nose |
| 4,655,771 A | 4/1987 | Wallsten |
| 4,714,460 A | 12/1987 | Calderon |
| 4,738,740 A | 4/1988 | Pinchuk et al. |
| 4,800,016 A | 1/1989 | Yang |
| 4,840,542 A | 6/1989 | Abbott |
| 4,883,459 A | 11/1989 | Calderon |
| 4,892,518 A | 1/1990 | Cupp |
| 5,030,199 A | 7/1991 | Barwick |
| 5,071,407 A | 12/1991 | Termin et al. |
| 5,084,015 A | 1/1992 | Moriuchi |
| 5,234,425 A | 8/1993 | Fogarty |
| 5,397,307 A | 3/1995 | Goodin |
| 5,411,478 A | 5/1995 | Stillabower |
| 5,419,763 A | 5/1995 | Hildebrand |
| 5,484,412 A | 1/1996 | Pierpont |
| 5,496,277 A | 3/1996 | Termin et al. |
| 5,607,466 A | 3/1997 | Imbert et al. |
| 5,668,237 A | 9/1997 | Popall |
| 5,688,237 A | 11/1997 | Rozga |
| 5,725,571 A | 3/1998 | Imbert et al. |
| 5,755,769 A | 5/1998 | Richard et al. |
| 5,759,205 A | 6/1998 | Valentini |
| 5,810,789 A | 9/1998 | Powers |
| 5,836,905 A | 11/1998 | Lemelson et al. |
| 5,836,967 A | 11/1998 | Schneider |
| 5,893,869 A | 4/1999 | Barnhart |
| 5,895,399 A | 4/1999 | Barbut |
| 5,897,567 A | 4/1999 | Ressemann |
| 5,910,154 A | 6/1999 | Tsugita |
| 5,911,734 A | 6/1999 | Tsugita |
| 5,957,974 A | 9/1999 | Thompson et al. |
| 6,001,118 A | 12/1999 | Daniel |
| 6,010,522 A | 1/2000 | Barbut |
| 6,027,520 A | 2/2000 | Tsugita |
| 6,042,598 A | 3/2000 | Tsugita |
| 6,051,014 A | 4/2000 | Jang |
| 6,059,745 A | 5/2000 | Gelbfish |
| 6,152,946 A | 11/2000 | Broome |
| 6,165,199 A | 12/2000 | Barbut |
| 6,165,200 A | 12/2000 | Tsugita |
| 6,168,579 B1 | 1/2001 | Tsugita |
| 6,179,851 B1 | 1/2001 | Barbut |
| 6,231,551 B1 | 5/2001 | Barbut |
| 6,235,044 B1 | 5/2001 | Root |
| 6,258,120 B1 | 7/2001 | McKenzie |
| 6,306,074 B1 | 10/2001 | Waksman |
| 6,306,163 B1 | 10/2001 | Fitz |
| 6,309,399 B1 | 10/2001 | Barbut |
| 6,361,545 B1 | 3/2002 | Macoviak |
| 6,371,969 B1 | 4/2002 | Tsugita |
| 6,371,971 B1 | 4/2002 | Tsugita |
| 6,383,206 B1 | 5/2002 | Gillick |
| 6,395,014 B1 | 5/2002 | Macoviak |
| 6,416,495 B1 | 7/2002 | Kriesel |
| 6,436,112 B2 | 8/2002 | Wensel |
| 6,443,926 B1 | 9/2002 | Kletschka |
| 6,478,783 B1 | 11/2002 | Moorehead |
| 6,485,456 B1 | 11/2002 | Kletschka |
| 6,485,502 B2 | 11/2002 | Don Michael |
| 6,499,487 B1 | 12/2002 | McKenzie |
| 6,500,203 B1 | 12/2002 | Thompson et al. |
| 6,520,183 B2 | 2/2003 | Amar |
| 6,530,935 B2 | 3/2003 | Wensel |
| 6,533,800 B1 | 3/2003 | Barbut |
| 6,537,294 B1 | 3/2003 | Boyle |
| 6,537,297 B2 | 3/2003 | Tsugita |
| 6,540,722 B1 | 4/2003 | Boyle |
| 6,551,303 B1 | 4/2003 | Van Tassel |
| 6,565,552 B1 | 5/2003 | Barbut |
| 6,569,146 B1 | 5/2003 | Werner |
| 6,582,396 B1 | 6/2003 | Parodi |
| 6,589,264 B1 | 7/2003 | Barbut et al. |
| 6,592,546 B1 | 7/2003 | Barbut et al. |
| 6,607,506 B2 | 8/2003 | Kletschka |
| 6,620,148 B1 | 9/2003 | Tsugita |
| 6,635,070 B2 | 10/2003 | Leeflang |
| 6,641,553 B1* | 11/2003 | Chee ............... A61B 17/32037 604/68 |
| 6,641,572 B2 | 11/2003 | Cherkassky |
| 6,645,220 B1 | 11/2003 | Huter |
| 6,645,222 B1 | 11/2003 | Parodi |
| 6,645,223 B1 | 11/2003 | Boyle |
| 6,652,555 B1 | 11/2003 | VanTassel |
| 6,652,556 B1 | 11/2003 | VanTassel |
| 6,656,351 B2 | 12/2003 | Boyle |
| 6,673,090 B2 | 1/2004 | Root et al. |
| 6,676,682 B1 | 1/2004 | Tsugita |
| 6,689,150 B1 | 2/2004 | VanTassel |
| 6,692,508 B2 | 2/2004 | Wensel |
| 6,692,509 B2 | 2/2004 | Wensel |
| 6,692,513 B2 | 2/2004 | Streeter |
| 6,695,813 B1 | 2/2004 | Boyle |
| 6,695,858 B1 | 2/2004 | Dubrul |
| 6,699,231 B1* | 3/2004 | Sterman ............ A61B 17/12045 604/509 |
| 6,702,834 B1 | 3/2004 | Boylan |
| 6,706,053 B1 | 3/2004 | Boylan |
| 6,706,055 B2 | 3/2004 | Douk |
| 6,730,108 B2 | 5/2004 | VanTassel |
| 6,746,469 B2 | 6/2004 | Mouw |
| 6,746,489 B2 | 6/2004 | Dua et al. |
| 6,802,317 B2 | 10/2004 | Goebel |
| 6,818,006 B2 | 11/2004 | Douk |
| 6,830,579 B2 | 12/2004 | Barbut |
| 6,837,898 B2 | 1/2005 | Boyle |
| 6,855,154 B2 | 2/2005 | Abdel-Gawwad |
| 6,866,677 B2 | 3/2005 | Douk |
| 6,887,258 B2 | 5/2005 | Denison |
| 6,896,690 B1 | 5/2005 | Lambrecht |
| 6,902,540 B2 | 6/2005 | Dorros |
| 6,908,474 B2 | 6/2005 | Hogendijk et al. |
| 6,911,036 B2 | 6/2005 | Douk |
| 6,936,060 B2 | 8/2005 | Hogendijk |
| 6,939,362 B2 | 9/2005 | Boyle |
| 6,964,670 B1 | 11/2005 | Shah |
| 6,964,673 B2 | 11/2005 | Tsugita |
| 6,974,469 B2 | 12/2005 | Broome |
| 6,989,027 B2 | 1/2006 | Allen |
| 6,997,898 B2 | 2/2006 | Forman |
| 7,044,958 B2 | 5/2006 | Douk |
| 7,044,966 B2 | 5/2006 | Svanidze |
| 7,066,946 B2 | 6/2006 | Douk |
| 7,101,396 B2 | 9/2006 | Artof |
| 7,118,600 B2 | 10/2006 | Dua et al. |
| 7,162,303 B2 | 1/2007 | Levin |
| 7,169,164 B2 | 1/2007 | Borillo |
| 7,172,614 B2 | 2/2007 | Boyle |
| 7,172,621 B2 | 2/2007 | Theron |
| 7,214,237 B2 | 5/2007 | Don Michael |
| 7,217,255 B2 | 5/2007 | Boyle |
| 7,223,253 B2 | 5/2007 | Hogendijk |

(56) References Cited

U.S. PATENT DOCUMENTS

| | | |
|---|---|---|
| 7,232,452 B2 | 6/2007 | Adams |
| 7,232,453 B2 | 6/2007 | Shimon |
| 7,241,304 B2 | 7/2007 | Boyle |
| 7,250,041 B2 | 7/2007 | Chiu |
| 7,252,675 B2 | 8/2007 | Denison |
| 7,279,000 B2 | 10/2007 | Cartier |
| 7,306,575 B2 | 12/2007 | Barbut |
| 7,322,957 B2 | 1/2008 | Kletschka |
| 7,326,226 B2 | 2/2008 | Root et al. |
| 7,331,973 B2 | 2/2008 | Gesswein |
| 7,338,510 B2 | 3/2008 | Boylan |
| 7,344,549 B2 | 3/2008 | Boyle |
| 7,364,566 B2 | 4/2008 | Elkins |
| 7,371,249 B2 | 5/2008 | Douk |
| 7,425,215 B2 | 9/2008 | Boyle et al. |
| 7,503,904 B2 | 3/2009 | Choi |
| 7,537,600 B2 | 5/2009 | Eskuri |
| 7,544,202 B2 | 6/2009 | Cartier |
| 7,572,272 B2 | 8/2009 | Denison |
| 7,582,100 B2 | 9/2009 | Johnson |
| 7,585,309 B2 | 9/2009 | Larson |
| 7,591,832 B2 | 9/2009 | Eversull |
| 7,604,650 B2 | 10/2009 | Bergheim |
| 7,647,115 B2 | 1/2010 | Levin |
| 7,653,438 B2 | 1/2010 | Deem |
| 7,658,747 B2 | 2/2010 | Forde |
| 7,686,781 B2 | 3/2010 | Vinten-Johansen |
| 7,833,242 B2 | 11/2010 | Gilson |
| 7,842,084 B2 | 11/2010 | Bicer |
| 7,846,139 B2 | 12/2010 | Zinn |
| 7,853,333 B2 | 12/2010 | Demarais |
| 7,873,417 B2 | 1/2011 | Demarais |
| 7,922,691 B2 | 4/2011 | Kletchka |
| 7,935,075 B2 | 5/2011 | Tockman |
| 7,937,143 B2 | 5/2011 | Demarais |
| 7,938,799 B2 | 5/2011 | Epstein |
| 7,993,324 B2 | 8/2011 | Barbut |
| 8,162,879 B2 | 4/2012 | Hattangadi et al. |
| 8,172,792 B2 | 5/2012 | Wang et al. |
| 8,182,446 B2 | 5/2012 | Schaeffer et al. |
| 8,200,312 B2 | 6/2012 | Degani |
| 8,251,948 B2 | 8/2012 | Goldman |
| 8,257,384 B2 | 9/2012 | Bates |
| 8,262,611 B2 | 9/2012 | Teesllink |
| 8,397,578 B2 | 3/2013 | Miesel |
| 8,409,166 B2 | 4/2013 | Wiener |
| 8,500,775 B2 | 8/2013 | Chomas |
| 8,696,698 B2 | 4/2014 | Chomas et al. |
| 8,696,699 B2 | 4/2014 | Chomas |
| 8,821,476 B2 | 9/2014 | Agah et al. |
| 8,852,207 B2 | 10/2014 | Simpson |
| 9,023,010 B2 | 5/2015 | Chiu |
| 9,061,117 B2 | 6/2015 | Roberts |
| 9,078,982 B2 | 7/2015 | Lane |
| 9,089,341 B2 | 7/2015 | Chomas |
| 9,126,016 B2 | 9/2015 | Chomas |
| 9,174,020 B2 | 11/2015 | Allen |
| 9,205,226 B2 | 12/2015 | Allen |
| 9,265,914 B2 | 2/2016 | Fulton, III |
| 9,364,358 B2 | 6/2016 | Cohen |
| 9,457,171 B2 | 10/2016 | Agah et al. |
| 9,463,304 B2 | 10/2016 | Agah et al. |
| 9,474,533 B2 | 10/2016 | Mathis |
| 9,539,081 B2 | 1/2017 | Chomas |
| 9,550,046 B1 | 1/2017 | Allen |
| 9,597,480 B2 | 3/2017 | Purdy |
| 9,604,037 B2 | 3/2017 | Fischer, Jr. |
| 9,770,319 B2 | 9/2017 | Pinchuk |
| 9,808,332 B2 | 11/2017 | Chomas |
| 9,844,383 B2 | 12/2017 | Allen |
| 9,913,959 B2 | 3/2018 | Purdy |
| 9,968,740 B2 | 5/2018 | Pinchuk |
| 10,092,742 B2 | 10/2018 | Genstler |
| 10,099,040 B2 | 10/2018 | Agah |
| 10,130,762 B2 | 11/2018 | Allen |
| 2002/0042593 A1* | 4/2002 | Mickley ............... A61M 29/02 604/102.01 |
| 2002/0161390 A1 | 10/2002 | Mouw |
| 2002/0161394 A1 | 10/2002 | Macoviak |
| 2003/0097114 A1 | 5/2003 | Duriel |
| 2003/0125790 A1 | 7/2003 | Fastovsky |
| 2003/0187474 A1 | 10/2003 | Keegan |
| 2003/0212361 A1 | 11/2003 | Boyle |
| 2003/0233115 A1 | 12/2003 | Eversull et al. |
| 2004/0054315 A1 | 3/2004 | Levin |
| 2004/0068288 A1 | 4/2004 | Palmer |
| 2004/0143185 A1 | 7/2004 | Zatezalo |
| 2004/0215142 A1 | 10/2004 | Matheis |
| 2004/0220511 A1 | 11/2004 | Scott |
| 2004/0220521 A1 | 11/2004 | Barbut |
| 2004/0220609 A1 | 11/2004 | Douk |
| 2004/0225354 A1 | 11/2004 | Allen |
| 2004/0256584 A1 | 12/2004 | Zimmerling |
| 2004/0260333 A1 | 12/2004 | Dubral |
| 2005/0004517 A1 | 1/2005 | Courtney et al. |
| 2005/0010285 A1 | 1/2005 | Lambrecht |
| 2005/0015048 A1 | 1/2005 | Chiu |
| 2005/0015112 A1 | 1/2005 | Cohn |
| 2005/0119688 A1 | 6/2005 | Burgheim |
| 2005/0149112 A1 | 7/2005 | Barbut |
| 2005/0261759 A1 | 11/2005 | Lambrecht |
| 2006/0124140 A1 | 6/2006 | Forsell |
| 2006/0167537 A1 | 7/2006 | Larsson |
| 2006/0173490 A1 | 8/2006 | LaFontaine |
| 2006/0177478 A1 | 8/2006 | Humes |
| 2006/0264898 A1 | 11/2006 | Beasley |
| 2007/0106324 A1 | 5/2007 | Gamer |
| 2007/0179590 A1 | 8/2007 | Lu |
| 2007/0239135 A9 | 10/2007 | Barbut |
| 2008/0031740 A1 | 2/2008 | Miyazaki |
| 2008/0031962 A1 | 2/2008 | Boyan |
| 2008/0033341 A1 | 2/2008 | Grad |
| 2008/0039786 A1 | 2/2008 | Epstein |
| 2008/0097273 A1 | 4/2008 | Levin |
| 2008/0103523 A1 | 5/2008 | Chiu |
| 2008/0147007 A1 | 6/2008 | Freyman |
| 2009/0018498 A1 | 1/2009 | Chiu |
| 2009/0076409 A1 | 3/2009 | Wu |
| 2009/0088676 A1 | 4/2009 | Murata |
| 2009/0198321 A1 | 8/2009 | Sutermeister |
| 2009/0222035 A1 | 9/2009 | Schneiderman |
| 2009/0234266 A1 | 9/2009 | Solomon |
| 2009/0234283 A1 | 9/2009 | Burton |
| 2009/0264819 A1 | 10/2009 | Diethrich et al. |
| 2010/0168785 A1 | 7/2010 | Parker |
| 2010/0331815 A1* | 12/2010 | Alt .................. A61K 38/21 604/507 |
| 2011/0046542 A1* | 2/2011 | Evans ............ A61B 17/320758 604/22 |
| 2011/0130657 A1 | 6/2011 | Chomas |
| 2011/0137399 A1 | 6/2011 | Chomas |
| 2011/0218494 A1 | 9/2011 | Gerrans |
| 2011/0288529 A1 | 11/2011 | Fulton |
| 2011/0295114 A1 | 12/2011 | Agah et al. |
| 2011/0295203 A1 | 12/2011 | Hayes |
| 2012/0116351 A1 | 5/2012 | Chomas |
| 2012/0259206 A1 | 10/2012 | Roberts |
| 2013/0079731 A1 | 3/2013 | Chomas |
| 2013/0116655 A1 | 5/2013 | Bacino |
| 2013/0226166 A1 | 8/2013 | Chomas |
| 2014/0066830 A1 | 3/2014 | Lad |
| 2014/0207178 A1 | 7/2014 | Chomas |
| 2014/0276135 A1 | 9/2014 | Agah et al. |
| 2014/0276411 A1 | 9/2014 | Cowan |
| 2014/0364835 A1* | 12/2014 | Allen ............... A61M 25/0068 604/509 |
| 2014/0378951 A1 | 12/2014 | Dye |
| 2015/0272716 A1 | 10/2015 | Pinchuk et al. |
| 2015/0306311 A1 | 10/2015 | Pinchuk et al. |
| 2016/0015948 A1 | 1/2016 | Agah et al. |
| 2016/0074633 A1 | 3/2016 | Schaffner |
| 2016/0082178 A1 | 3/2016 | Agah et al. |
| 2016/0235942 A1 | 8/2016 | Alt |
| 2016/0235950 A1 | 8/2016 | Murata |

(56) References Cited

U.S. PATENT DOCUMENTS

| | | | |
|---|---|---|---|
| 2016/0256626 A9 | 9/2016 | Chomas | |
| 2016/0310148 A1* | 10/2016 | Allen | A61B 17/12136 |
| 2017/0000493 A1 | 1/2017 | Boehm, Jr. | |
| 2017/0049946 A1 | 2/2017 | Kapur | |
| 2017/0056629 A1 | 3/2017 | Agah et al. | |
| 2017/0157370 A1* | 6/2017 | Agah | A61M 25/0097 |
| 2017/0173309 A1 | 6/2017 | Fischer, Jr. | |
| 2017/0209666 A1 | 7/2017 | Quigley | |
| 2017/0319820 A1 | 11/2017 | Johnson | |
| 2017/0368306 A1* | 12/2017 | Tal | A61B 17/12186 |
| 2018/0055620 A1 | 1/2018 | Chomas | |
| 2018/0116522 A1 | 5/2018 | Brenneman | |
| 2018/0125502 A1 | 5/2018 | Allen | |
| 2018/0250469 A1 | 9/2018 | Pinchuk | |
| 2018/0263752 A1 | 9/2018 | Pinchuk | |
| 2018/0289464 A1 | 10/2018 | Kassab | |
| 2018/0333563 A1 | 11/2018 | Agah | |
| 2019/0046157 A1 | 2/2019 | Unser | |
| 2019/0083705 A1 | 3/2019 | Allen | |
| 2020/0078555 A1 | 3/2020 | Agah | |

FOREIGN PATENT DOCUMENTS

| | | | |
|---|---|---|---|
| EP | 0554579 A1 | 8/1993 | |
| EP | 0416662 B1 | 3/1996 | |
| EP | 1226795 | 7/2002 | |
| EP | 1527740 | 5/2005 | |
| EP | 1803423 | 7/2007 | |
| EP | 1743524 A1 * | 1/2017 | A01K 67/027 |
| EP | 1743524 A1 * | 1/2017 | A01K 67/027 |
| FR | 2652267 A1 | 3/1991 | |
| GB | 2020557 B | 1/1983 | |
| WO | 8905667 | 6/1989 | |
| WO | 199916382 | 4/1999 | |
| WO | 199944510 A1 | 9/1999 | |
| WO | 200141679 | 6/2001 | |
| WO | 200145592 | 6/2001 | |
| WO | 200149215 A2 | 7/2001 | |
| WO | 0197879 | 12/2001 | |
| WO | 2004043293 | 5/2004 | |
| WO | WO2011/068946 A1 | 6/2011 | |

OTHER PUBLICATIONS

Search Report and Written Opinion dated Jan. 6, 2020 of application No. PCT/US 19/54406.
RenovoCath™ RC120 The Future of Targeted Delivery, RenovoRx Inc., web brochure downloaded from internet on Feb. 2, 2015.
Allogenic Chimeric Antigen Receptor-Modified Cells for Adoptive Cell Therapy of Cancer, Marcus, Assaf et al., Mar. 24, 2014, Expert Opinion of Biological Therapy, vol. 14, Issue 7.
A Study of the Geometrical and Mechanical Properties of a Self-Expandig Metallic Stent Theory and Experiment, Dr. Michael R. Jedwab, Claude 0. Clerc, Journal of Applied Biomaterials, vol. 4, Issue 1, pp. 77-85, Spring 1993.
U.S. Appl. No. 61/266,068, filed Dec. 2, 2009, Chomas et al.
U.S. Appl. No. 61/382,290, filed Sep. 13, 2010, Chomas et al.
Catheter-Based Renal Sympathetic Denervation for Resistant Hypertension: a Multicentre Safety and Proof-of-Principle Cohort Study, Krum et al, The Lancet, 2009.
Embolization II, Scientific Session 11, JVIR, Mar. 27, 2012.
Embolization procedure lowers levels of "hunger hormone," leads to weight loss, EurekAlert Public Release, Mar. 7, 2013.
Finite Element Stent Design, M. De Beule, R. Van Impe, P. Verdonck, B. Verhegghe, Computer Methods in Biomechanics and Biomedical Engineering, 2005.
First-In-Man Study of Left Gastric Artery Embolization for Weight Loss, Nicholas Kipshidze et al., Acc.13, E2056, UACC Mar. 12, 2013, vol. 61, Issue 10.
Fusion Drug Delivery System—Novel Catheter/Stent Design for Targeted Drug Delivery, Gerschwind & Barnett, Non-Published US provisional patent application filed Sep. 17, 2007.
International Search Report and Written Opinion of Application No. PCT/US16/23723 dated Sep. 2, 2016.
International Search Report of PCT/US18/22171 dated Aug. 3, 2018.
Left Gastric Embolization Leads to Weight Loss, Bariatriac News, Owen Haskins, Dec. 4, 2013.
Renal Denervation as a Therapeutic Approach for Hypertension: Novel Implications for an Old Concept, Schlaich et al., Hypertension, Journal of the American Heart Association, 2009, 54:1195-1201.
Renal Sympathetic-Nerve Ablation for Uncontrolled Hypertension, Schlaich et al, The New England Journal of Medicine, 2009, pp. 932-934, Aug. 27, 2009.
Cannulation of the Cardiac Lymphatic Sytem in Swine, Vazquez-Jiminez et al., European Journal of Cardio-thoracic Surgery 18 (2000) 223-232.
Development of Repeatable Microcatheter Access Port for Intra-arterial Therapy of Liver Cancer, Yasushi Fukuoka et al., Cardiovasc Intervent Radiol (2019) 42:298-303.
Long-Term Catheterization of the Intestinal Lymph Trunk and Collection of Lymph in Neonatal Pigs, Richard R. Uwiera et al., Journal of Visualized Experiments, Mar. 2016, 109, e53457.
Lymphaniography to Treat Postoperative Lymphatic Leakage: A Technical Review, Edward Wolfgang Lee, et al., Korean Journal of Radiology 15(6), Nov./Dec. 2014.
Radiologic Placement of Side-hole Catheter with Tip Fixation for Hepatic Arterial Infusion Chemotherapy, Toshihiro Tanaka et al., J Vasc Interv Radiol 2003: 14:63-68.
Superselective Retrograde Lymphatic Duct Embolization for Management of Postoperataive Lymphatic Leak, Bulent Arslan et al., Diagn Interv Radiol 2017; 23:379-380.
International Search Report and Written Opinion of Application No. PCT/US19/13482 dated Jun. 10, 2019.
Estimation of Tumor Interstitial Fluid Pressure (TIFP) Noninvasively, Long Lian Liu et al., PLOS One | DOI:10.1371/journal.pone. 0140892 Jul. 28, 2016.

* cited by examiner

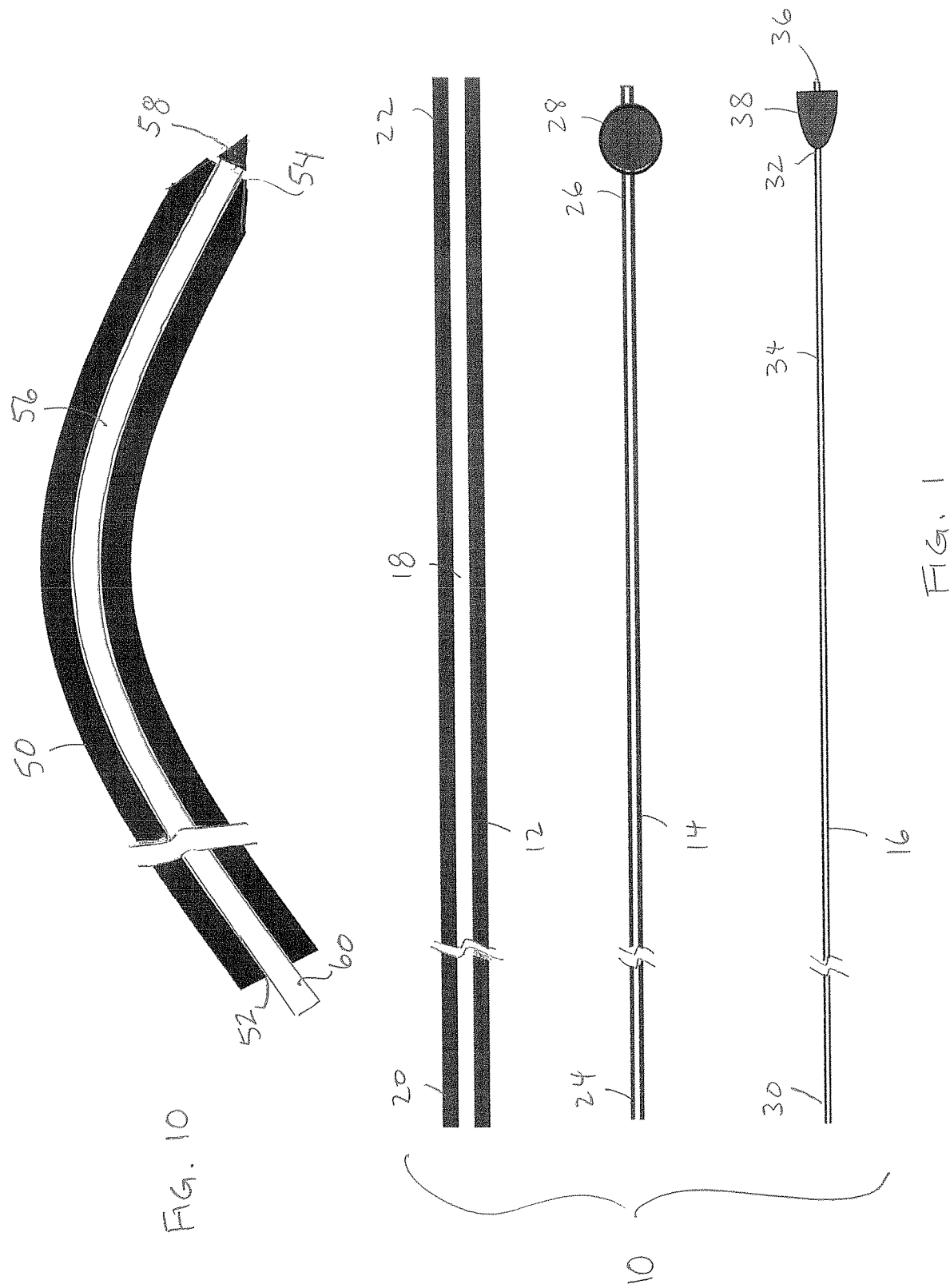

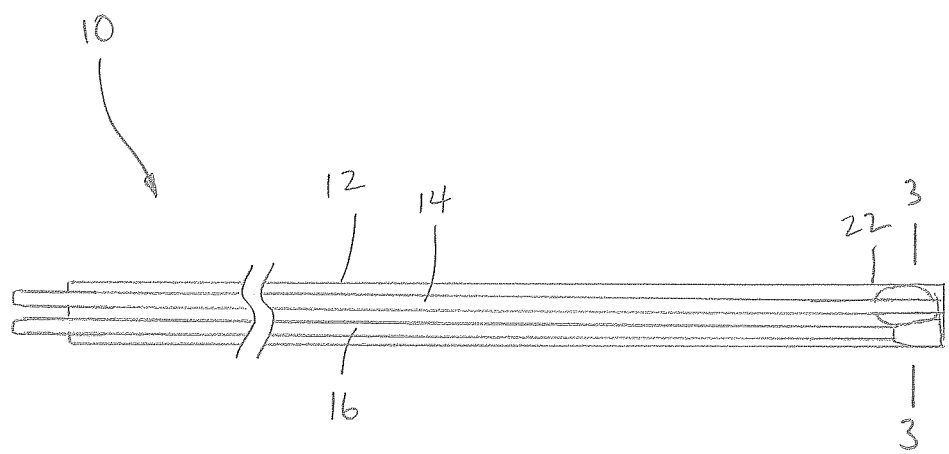
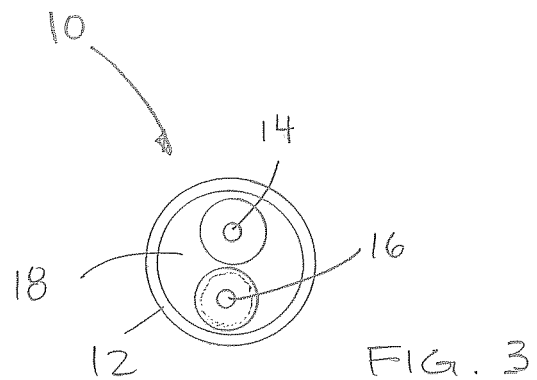

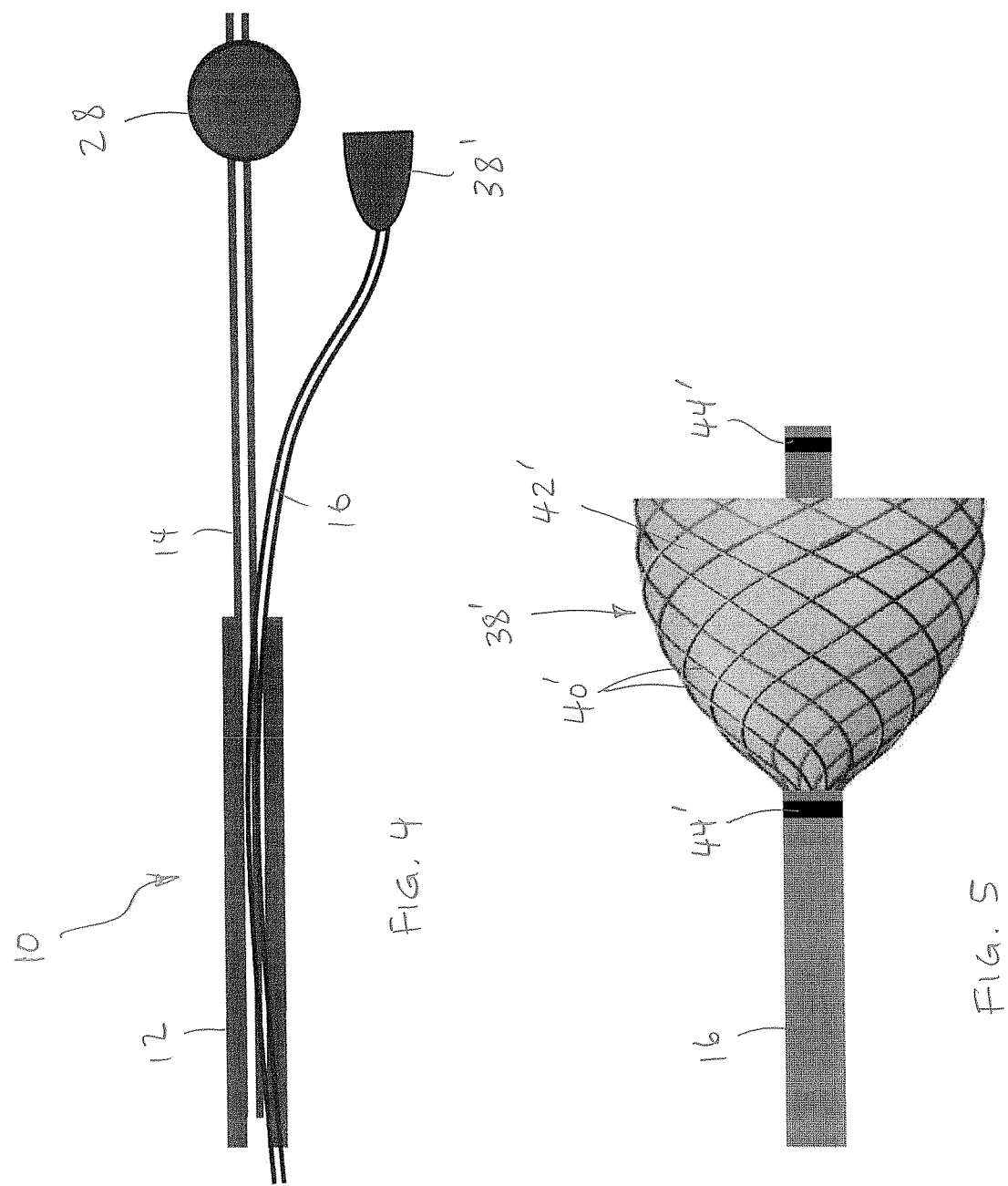

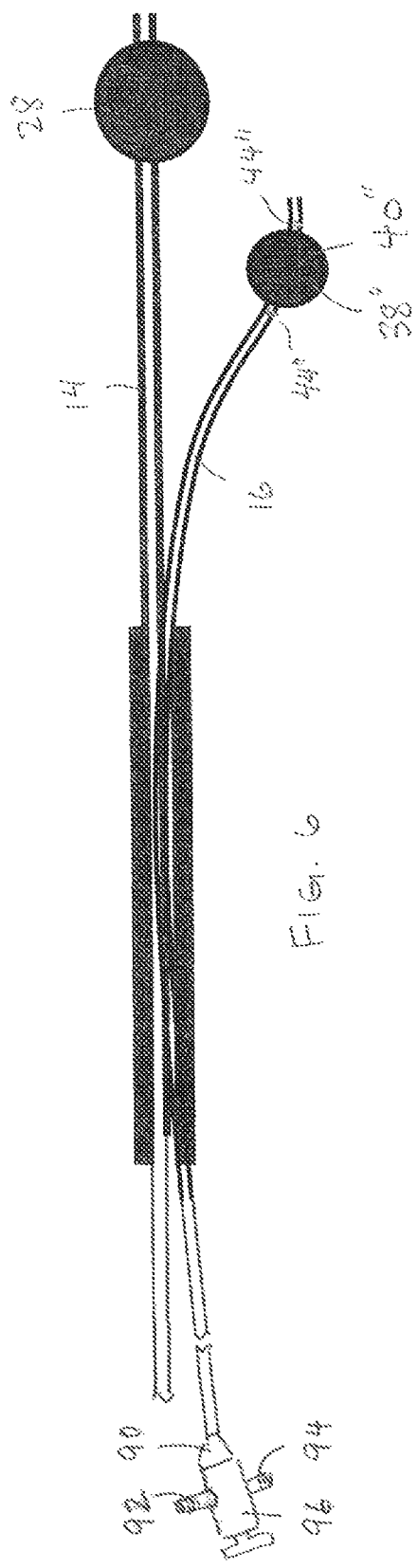
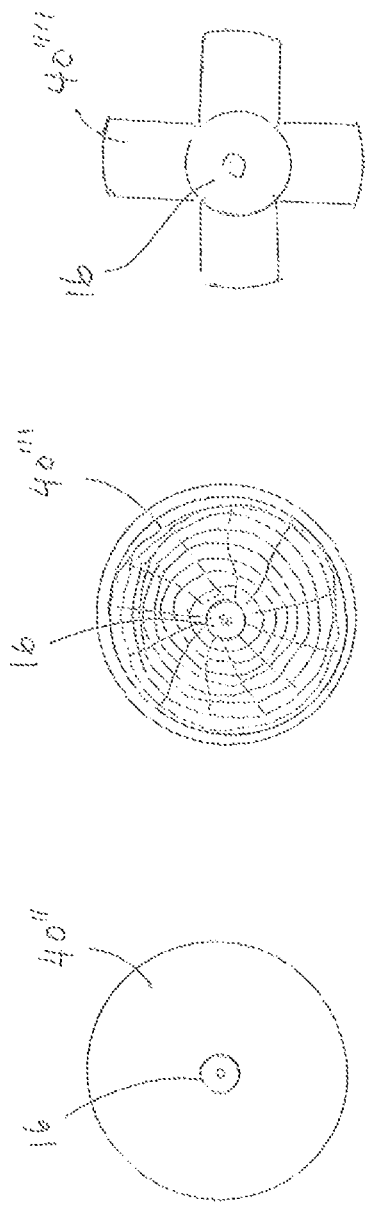

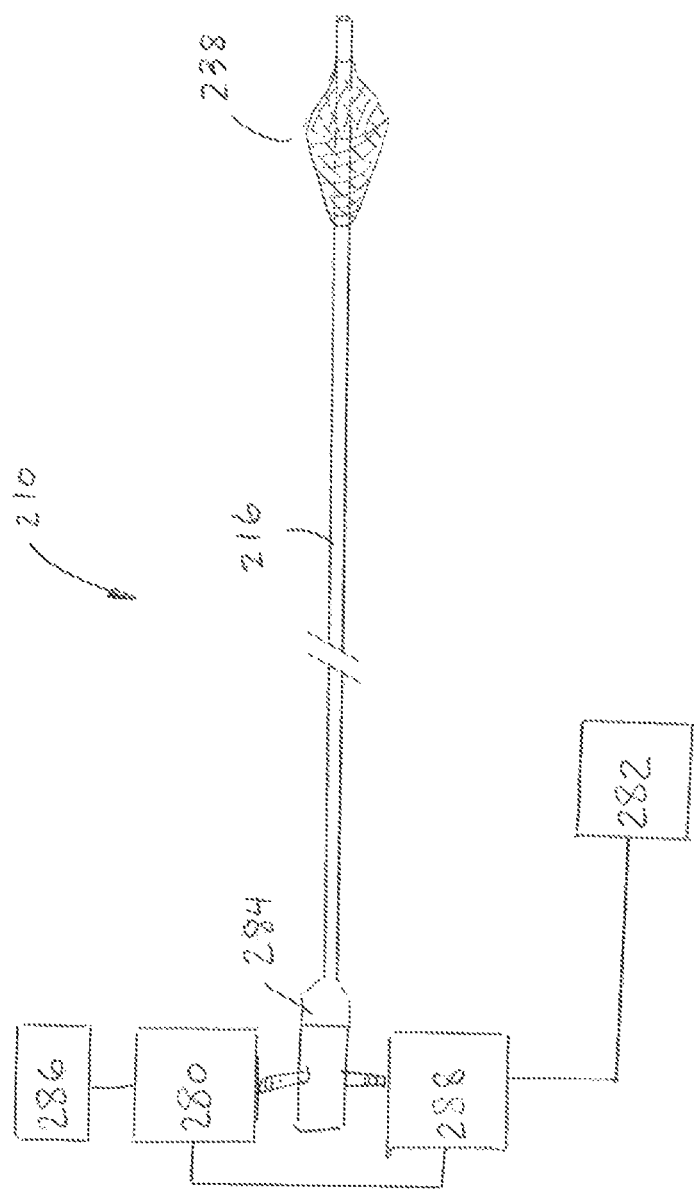

SYSTEM AND METHOD FOR SELECTIVE PRESSURE-CONTROLLED THERAPEUTIC DELIVERY

CROSS-REFERENCE TO RELATED APPLICATION

This application claims benefit to U.S. Provisional Application Ser. No. 62/396,622, filed Sep. 19, 2016, which is hereby incorporated by reference herein in its entirety.

BACKGROUND OF THE INVENTION

1. Field of the Invention

The medical devices and method described herein relate generally to medical devices and methods for infusing a treatment through a vessel to a target tissue for the treatment of cancer or other diseases.

2. State of the Art

In some instances, systemic treatments are used to treat disease within a patient. The effectiveness of some such systemic treatments can vary due at least in part to the treatment (e.g., a radio-embolization agent, a biologic agent and/or other treatment formulation) not reaching target tissue. For example, in the treatment of some diseases such as pancreatic cancer and/or diabetes, it may be desirable to deliver biological cells to the pancreas where efficient and safe engraftment can be achieved, especially to the pancreatic tail, for example, where a large number of the endogenous islet cells reside. Specifically, in some instances, some systemic treatments of diabetes, which affects the body's ability to produce and/or regulate insulin, have attempted to transplant insulin producing beta cells into pancreatic tissue, however, with limited success due to a lack of supply and a long term need for immunosuppression. In other forms of treatment for diabetes, transplantation of autologous stem cells (mesenchymal, bone marrow, and others) can increase and/or replace the supply of insulin, especially in Type II diabetes where autoimmune reaction against these cells appears limited. In such treatments, various methods have been used such as, for example, transplanting the cells surgically in the sub capsular space in the kidney, the liver, and nonselective systemic injection both intravenously and intra-arterially, with the hope of "homing" these cells to the pancreatic tissue to allow engraftment, however, a best mode of transplantation has yet to established.

In some instances, a treatment can include transplanting such cells into the pancreas itself. For example, one treatment has included sub-selective endovascular injection of these cells into the arterial supply of the pancreatic tissue. Such an approach, however, is subject to variation in the number of cells actually introduced to the pancreas (versus other organs in the same vascular bed including the spleen, the liver, and/or the stomach). Furthermore, inadvertent exposure of other non-target organs to such cells can result in health risks for the patient.

Treatments for pancreatic cancer can be similarly ineffective. For example, pancreatic cancer is considered an almost chemoresistant tumor. The ineffective result of systemic chemotherapy is at least in part due to an insufficient drug concentration within the tumor because of dose-limited toxicity in bone marrow and epithelial tissue. Since systemic chemotherapy is limited in its effectiveness, treatments beyond systemic chemotherapy can be desirable for advanced pancreatic cancer patients. For example, one such treatment can include local intra-arterial delivery of chemotherapy. Intra-arterial infusion allows higher drug concentration to reach the tumor. Furthermore, intra-arterial chemotherapy can also take advantage of the first pass effect of chemotherapeutics, generating higher-level drug concentrations at the tumor cell membrane and therefore, enhancing cellular drug uptake as compared to intravenous infusion. Lastly, local delivery can reduce systemic side effects.

Intra-arterial chemotherapy treatment is usually administered through small catheters placed in the celiac/hepatic artery or portal vein. An issue in catheter localization is the redundant nature of blood supply to the pancreas overlapping adjacent organs. Furthermore, the small size and anatomical variability of the branches of the hepatic and splenic arteries to the pancreas precludes reproducible cannulization via interventional techniques. Delivering the therapy to the correct location requires knowledge of the patient's arterial anatomy, preferably obtained through visualization techniques in advance of therapeutic delivery of the treatment.

Even then, standard catheters permit limited control of the infused treatment. The treatment will flow from an area of high pressure to an area of lower pressure. Given the cyclic pressure operating on the blood as the heart beats, the treatment can reflux into healthy tissues where it will do harm, rather than good.

In order to alleviate certain of these issues, co-owned U.S. Pat. No. 8,696,698 to Chomas describes a pressure-controlled therapeutic delivery device in the form of a microvalve mounted at the distal end of catheter. The microvalve dynamically expands and contracts within a blood vessel in relation to the surrounding blood pressure. A treatment can be infused through the catheter under significant pressure. When the treatment agent is infused, the pressure in the vessel downstream (distal) of the treatment is always higher than that upstream (proximal) of the treatment, causing the microvalve to open and block reflux of the agent.

One issue to using the Chomas pressure-controlled therapeutic delivery device for delivery of a therapeutic agent to the pancreas is that the portal vein, which extends through the pancreas, is open to the spleen. The spleen has the capacity to store a large volume of blood. As such, any therapeutic agent injected into the portal vein will travel to the spleen rather than into the smaller feeder vessels off of the portal vein. Therefore, the therapeutic agent may not reach desirable therapeutic concentrations deep within the pancreas, where needed.

US Pub. No. 2016/0082178 to Agah discloses a device and method for isolating and visualizing feeder vessels using an endovascular approach. The device includes an outer catheter and an inner catheter longitudinally displaceable in a telescoping arrangement. An occlusive element is coupled to each catheter. The outer catheter includes side openings, and an agent can be infused through the outer catheter and out of the side openings between the two occlusive elements. In use, the device is advanced to the portal vein, and the catheters are displaced to locate the occluders on opposing sides of feeder vessels. The occluders are then expanded to isolate a region of the portal vein containing the feeder vessels, thereby causing cessation of blood flow within the isolated region. Then a contrast agent is injected through the outer catheter, out the side openings, and into the portal vein, where it travels only within the isolated region of the portal vein and off to the feeder vessels of the portal vein to visualize the vessels. A similar subsequent step can be performed to inject a therapeutic agent into the portal vein and feeder vessels.

This system has several disadvantages. As the portal vein does not have significant tubular strength and can expand when subject to the increased pressure of the injected therapeutic agent, the agent may flow around the occluders and out into areas that are not intended to receive the agent. This would result in a reduced concentration of therapeutic agent in the feeder vessels where it is most needed and may also result in therapeutic agent travelling to and detrimentally acting upon unintended tissues. In addition, if the occluders are expanded to too large a size to attempt to prevent leakage, the vessels can be damaged. Further, the release of the therapeutic agent is into the portal vein; however, the size of the opening or openings in the catheter for release of the therapeutic agent is very small in relation to the diameter of the portal vein, further preventing generation of the pressure desired to saturate and penetrate the intended tissues with the therapeutic agent.

SUMMARY OF THE INVENTION

A system is provided for the treatment of an organ with a vascular-infused therapeutic agent. In an embodiment, the system includes an outer guide sheath having proximal and distal ends, a first catheter longitudinally displaceable within the outer guide sheath and provided with a first distal occlusion device, and a second catheter longitudinally displaceable within the outer guide sheath and provided with a second distal occlusion device.

In an embodiment, the first and second catheters are arranged parallel and non-coaxial within the guide sheath.

In another embodiment, the second catheter extends parallel and coaxially within a portion of the first catheter, but the first catheter is adapted permit the second catheter to extend outside the first catheter at a location proximal of the first distal occlusion device so that the first and second distal occlusion devices are non-coaxial in a treatment configuration.

In an embodiment, the first distal occlusion device is preferably a balloon sized to be inserted into the splenic vein and has an expanded configuration in which it extends across the splenic vein to block fluid flow thereby.

In an embodiment, the second distal occlusion device has an expanded configuration sized to extend across a small feeder vessel branching from the splenic vein, and the second catheter is adapted to deliver therapeutic agent out of an orifice located at the distal end of the second catheter to exit on a distal side of the second occlusion device. The second occlusion device preferably, at least in use and optionally in design and structure, expands to a smaller maximum diameter than the first occlusion device, as it is intended for use in a smaller vessel (feeder vessels) than the first occlusion device is intended (the splenic vein).

In an embodiment, the system is limited to the second occlusion device, alone, without the first occlusion device.

The second occlusion device is configured to permit injection of a infusate under relatively high pressure; i.e., a pressure-control element. The pressure-control element may be a dynamic device or a static device. A dynamic pressure-control element may include a microvalve that automatically expands to the diameter of the vessel in which it is deployed when subject to predetermined fluid pressure conditions and contracts to a smaller diameter when subject to relatively lower fluid pressure conditions. A microvalve suitable for use preferably includes a microporous polymer advantageously formed by electrospinning or dip-coating a polymer over a filamentary braid having a frustoconical portion. The microporous polymer allows generation of fluid pressure at one side of the microvalve, while blocking particles on the pressurized side of the microvalve that exceed 5 µm from passing through the microvalve.

A static pressure-control element includes a fluid inflatable balloon, a self-expanding filter, and a mechanically expandable malecot catheter. These elements cause occlusion of the vessel by being sufficiently expanded to block flow within a vessel around the static pressure-controlled element, and do not modulate in expansion in view of localized fluid pressure conditions within the vessel.

In an embodiment, the system also includes a pressure-detecting element and/or an infusion timing element adapted to permit injection of the infusate based on a localized pressure or timing event.

In an embodiment, such pressure-detecting element permits injection of the infusate during an intended blood pressure, change in blood pressure, or at a prescribed time delay relative to a change in pressure at the heart or in the target organ. The pressure-detecting element can, e.g., permit or activate infusion during the diastolic period and halt or deactivate infusion during the systolic period; this increases pressure differential and maximizes organ uptake of the infusate. By way of example, the pressure-detecting element may include a pressure sensor and optionally a pump.

In an embodiment, the infusion timing element is adapted to permit injection of the infusate at a set time offset following a portion of the cycle of the heart rate, with such delay capable of accounting for a consequent change in pressure occurring in the target organ after a pressure change at the heart. By way of example, the timing element may include a connection to an EKG or pulse-oximeter and optionally a pump.

The system may also include an access needle provided with a piercing tip and a distal opening. The access needle may be curved. The piercing tip may be in the form of a removable obturator, which when removed exposes the distal opening. The piercing tip is configured and sized to directly pierce the portal vein and enter into the interior of the portal vein in a manner that communicates the distal opening of the access needle with the interior of the portal vein. In an embodiment, the access needle includes a lumen sized to permit longitudinal passage of the guide sheath therethrough. The system may also include an exchange device to facilitate displacement of the access needle over the guide sheath, particularly after the guide sheath has been inserted into the portal vein.

In one embodiment of use, the access needle is deployed directly into the portal vein without traversing other endo-vascular vessels. This is achieved by directly puncturing the portal vein with the aid of ultrasound visualization.

The first catheter is then advanced out of the guide catheter, through the portal vein and into the splenic vein traversing the pancreas and toward the spleen. Once the first occlusion device on the first catheter is at the end of the splenic vein adjacent the spleen, the first occlusion device is expanded to occlude the splenic vein.

A contrast agent is then infused through the guide catheter (either around the first and second catheters, or within a dedicated lumen) and out into the portal vein and to the splenic vein providing visualization of the splenic vein and feeder vessels extending off of the splenic vein and deep into the pancreas. The first occlusion device may then remain in the expanded state, or more preferably is contracted via deflation to again permit blood flow within the splenic vein up to the portal vein. A guidewire is then advanced through the second catheter and, under guidance of the imaging provided by the contrast agent, guided into a first feeder vessel extending from the splenic vein.

The second catheter is then advanced over the guidewire so that the second occlusion device is at or beyond the ostium of the first feeder vessel. If the second occlusion device is a static device, it is then expanded to block passage within the first feeder vessel. If the second occlusion device is dynamic no pre-expansion is required, as the second occlusion device will automatically expand when subject to the increased fluid pressure of the injected treatment agent.

The treatment agent is then injected under pressure through the second catheter and into the feeder vessel. When the pressure within the feeder vessel is higher than the systemic pressure and the second occluder device is expanded open into atraumatic contact with the vessel wall, the treatment agent is prevented from flow outside the region of the feeder vessel and is forced deep into the pancreatic tissue. Another way to increase the pressure is by providing the second catheter in a diameter that approaches the size the feeder vessel so that a large pressure head can be developed. Yet another way in which this may be accomplished is by adapting the second occlusion device so that it can automatically accommodate the size of the vessel wall, even if the vessel wall expands in diameter. These approaches can be used individually or in combination.

In an embodiment of use, the blood pressure or a change in blood pressure is detected and the treatment agent is injected through the second catheter only sensing that the pressure in the target organ or at the heart meets a sensed condition. Once the condition is met, the system may permit manual injection or may include a pump that automatically injects the treatment agent.

In another embodiment of use, combinable with the aforementioned method or used without, the treatment agent is injected after a prescribed time following a sensed condition. At the prescribed time following the sensed condition, the system may permit manual injection or may include a pump that automatically injects the treatment agent.

In an embodiment, the infusion timing element is adapted to permit injection of the infusate at a set time offset following a portion of the cycle of the heart rate, with such delay capable of accounting for a consequent change in pressure occurring in the target organ after a pressure change at the heart. By way of example, the timing element may include a connection to an EKG or pulse-oximeter and optionally a pump.

BRIEF DESCRIPTION OF THE DRAWINGS

FIG. 1 is a schematic illustration of a kit that can be assembled into a treatment system for performing pressure-controlled therapeutic delivery.

FIG. 2 is a schematic illustration of an embodiment of the assembled system in which the first and second catheters extend within a guide catheter.

FIG. 3 is cross-section across line 3-3 in FIG. 2.

FIG. 4 is a schematic illustration of one embodiment of a treatment system for performing pressure-controlled therapeutic delivery.

FIG. 5 is a dynamic occlusion element of the treatment system shown in FIG. 4.

FIG. 6 is a schematic illustration of another embodiment of a treatment system for performing pressure-controlled therapeutic delivery.

FIG. 7 is a first static occlusion element for the treatment system shown in FIG. 6.

FIG. 8 is a first static occlusion element for the treatment system shown in FIG. 6.

FIG. 9 is a first static occlusion element for the treatment system shown in FIG. 6.

FIG. 10 is a schematic illustration of an access needle of a kit and system for performing pressure-controlled therapeutic delivery.

FIG. 17 is a schematic illustration of another embodiment of a treatment system for performing pressure-controlled therapeutic delivery.

DETAILED DESCRIPTION OF THE PREFERRED EMBODIMENTS

Figure 11:
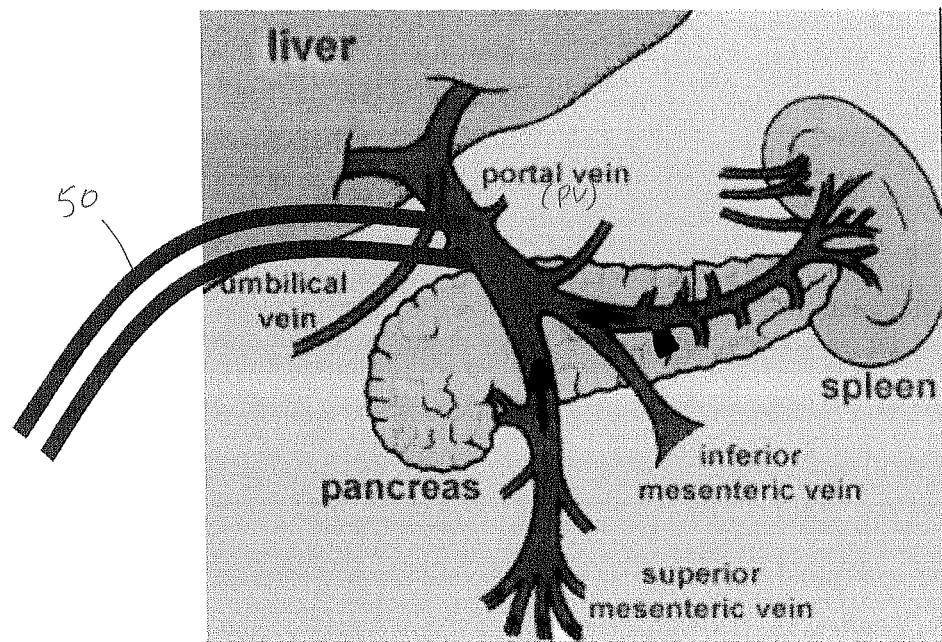
FIGS. 11 through 14 illustrate a method for performing pressure-controlled therapeutic delivery.

With reference to the following description, the terms "proximal" and "distal" are defined in reference to the hand of a user of the devices and systems described herein, with the term "proximal" being closer to the user's hand, and the term "distal" being further from the user's hand such as to often be located further within a body of the patient during use.

Apparatus and methods are described herein related to the use of a system to inject a contrast agent into a primary vessel and use the visualization provided by the contrast agent to identify feeder vessels leading from the primary vessel and communicating with, for example, a tumor or to identify one or more feeder vessels leading to a site of vasculature bleeding. For example, the tumor to be treated can be a solid tumor. In some cases, the tumor can be a cancerous tumor, such as a tumor specific to, for example, cancer of the pancreas, colon, liver, lung, or uterus.

As described herein, a treatment system is used to provide a treatment agent around, for example, a solid tumor, to permit targeted treatment of a region by the treatment agent, isolation of the treatment agent within the target region, all without isolating a larger region than necessary from blood flow during the treatment procedure. In some cases, the solid tumor is associated with cancer of the pancreas, colon, liver, lung or uterus. With the treatment system in place, the treatment agent (e.g., an immunotherapy agent, chemoembolization agent, radio-embolization agent, in combination with a contrast dye) can be injected under pressure into a region of an organ or other defined area of tissue served by one or more feeder vessels. As such, the treatment system is used to identify small tumor feeder vessels connected to a tumor and selectively inject a treatment agent under pressure into the small tumor feeders.

In embodiments, the method includes introducing a treatment system into a target vessel within a patient where the target vessel is near a tumor. The target vessel may be an artery or vein. The target vessel may lead or extend within any of various organs, including, but not limited to, the pancreas, colon, liver, lung or uterus. In embodiments, the treatment system may be introduced into or adjacent the target vessel non-endovascularly. Particularly, the treatment system may be introduced into the target vessel or into an adjacent vessel communicating with the target vessel directly through an access needle.

Referring now to FIGS. 1, 2 and 3, an embodiment of the treatment system 10 includes an outer guide sheath 12, and a first catheter 14 and a second catheter 16. The guide sheath 12 has proximal and distal ends 20, 22, and a lumen 18 extending between its ends. The first and second catheters 14, 16 are arranged parallel and preferably non-coaxial within the lumen 18 of the guide sheath 12, and are longitudinally displaceable relative to guide sheath such that each can be extended out of the distal end 22, and retracted back into the lumen 18 of the guide sheath. The first catheter 14 has proximal and distal ends 24, 26, and is provided with a first distal occlusion device 28 at its distal end 26. The second catheter 16 has proximal and distal ends 30, 32, and a lumen 34 extends therethrough. A distal pressure-control element 38 is mounted at the distal end 32, and a distal orifice 36 of the lumen opens distally of the pressure-control element 38. The first distal occlusion device 28 and pressure-control element 38 can be advanced into vessels branched relative to each other; i.e., the first distal occlusion device 28 can be positioned within a primary vessel while the distal pressure-control element 38 is positioned within a feeder vessel thereof, as discussed in detail below.

Figure 16:
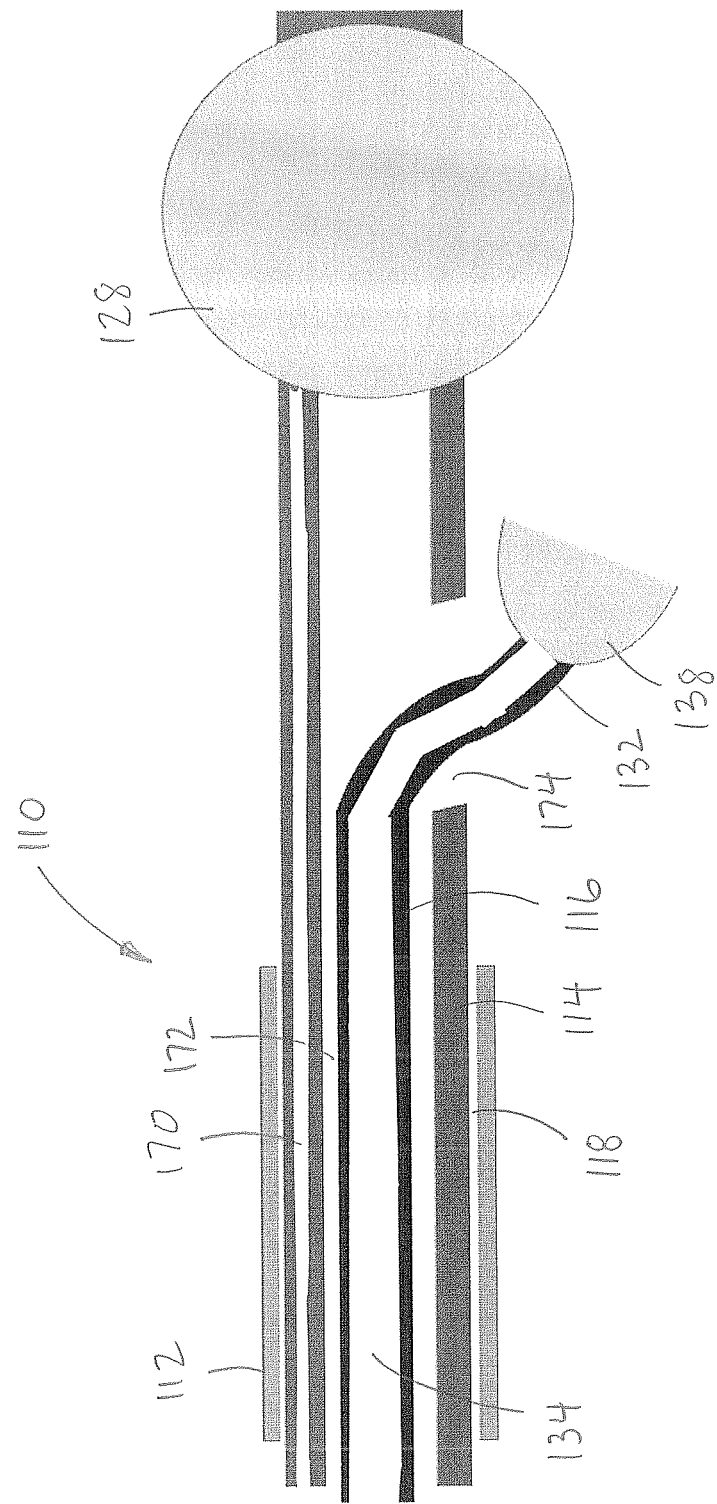
FIG. 16 is a schematic illustration of an alternate embodiment of the system in which the first and second catheters extend within a guide catheter, showing the second catheter traversing outside of the first catheter.

Turning now to FIG. 16, the distal end of an alternate embodiment of the treatment system 110 (with like parts having reference numerals incremented by 100) is shown. The treatment system includes an outer guide sheath 112, a first catheter 114, and a second catheter 116. The guide sheath 112 has a lumen 118 through which the first and second catheters 112, 114 are introduced. The first catheter includes a first lumen 170 extending to the first distal occlusion device (for inflation thereof) 128, and a second lumen 172 having a side opening 174 at a location proximal of the first distal occlusion device 128. The second catheter 116 has a lumen 134 extending through its distal pressure-control element 138 mounted at the distal end 132. The second lumen 172 and side opening 174 are sized to receive the distal pressure-control element 138 and second catheter 116 therethrough. The second catheter can be displaced through the second lumen of the first catheter 114 and advanced out of the side opening 174 so that the first distal occlusion device 128 and pressure-control element 138 can be advanced into separate and branched vessels. The following description of the treatment system 10 equally applies to this embodiment of the treatment system 110.

The first occlusion device 28 on the first catheter 14 is preferably a balloon sized to be inserted into the portal vein along a portion thereof between the liver and the pancreas, and has an expanded configuration in which it is sized to extend across the splenic vein to completely block fluid flow along the splenic vein to/from the spleen.

The pressure-control element 38 on the second catheter 16 includes an expanded configuration that is sized to extend across a small feeder vessel branching from the splenic vein, and the second catheter 16 is adapted to deliver therapeutic agent through the lumen 34 and out of the orifice 36 to exit on a distal side of the pressure-control element 38. The pressure-control element 38 preferably, at least in use and optionally in design and structure, expands to a smaller maximum diameter than the first occlusion device 28, as it is intended for expansion within smaller vessels (feeder vessels off of the splenic vein) than the first occlusion device 28 is intended (the splenic vein itself).

The pressure-control element 38 may be a dynamic device or a static device. As shown in FIGS. 1 to 3, and 4 and 5, an embodiment of a dynamic pressure-control element includes a microvalve 38' that automatically expands to the diameter of the vessel in which it is deployed when subject to predetermined fluid pressure conditions and collapses to a smaller diameter when subject to relatively lower fluid pressure conditions. The second catheter 16 extends coaxially into or through the microvalve 38'. Radiopaque markers 44' may be provided on the catheter or microvalve to provide fluoroscopic visualization of the microvalve 38' in use. A microvalve 38' suitable for use preferably includes a filamentary braid 40' coated with a microporous polymer 42'. The microporous polymer 42' allows generation of fluid pressure at one side of the microvalve 38', while blocking particles on the pressurized side of the microvalve that exceed 5 µm from passing through the microvalve. The braid 40' preferably expands into a frustoconical form.

The braid 40' is made from metal filaments, polymer filaments, ceramic filaments, glass filaments, radiopaque oxides, or a combination of metal and polymer filaments, which are formed into a substantially frustoconical shape when not subject to outside forces. Where metal filaments are used, the filaments are preferably elastic or superelastic metal such as stainless steel or shape memory nickel-titanium alloy (Nitinol). Where polymeric filaments are utilized, the filaments may be composed of polyethylene terephthalate (PET), polyethylene-napthalate (PEN), liquid crystal polymer, fluorinated polymers, nylon, polyamide or any other suitable polymer. The polymer filaments may be impregnated with a radiopaque agent such as barium sulfate, iodine compounds, radiopaque metallic particles, or other contrast agents to facilitate imaging of the filter valve during use. Iodinated polymeric materials may also be employed as the polymeric filaments.

It is desirable that the braid 40' be biased into an expanded configuration at a predetermined force. Therefore, when polymeric filaments are utilized, one or more metal filaments may be utilized in conjunction with the polymeric filaments to provide a desired expansion force to the braid. The diameter of one, more or all of the filaments also can be selected to control the expansion force. In addition, the braid angle can be altered to change the expansion force. Further, as indicated below, the thickness of the polymer coating can be adjusted to alter the expansion force.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0} \quad K_2 = \frac{2\cos^2\beta_0}{D_0} \quad K_3 = \frac{D_0}{\cos\beta_0},$$

and I and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), stent diameter ($D_0$), and number of filaments (n) impact the radial force of the braided valve.

The filaments of the braid 40' are not bonded to each other along their lengths to allow the element 38 to rapidly open and close in response to dynamic flow conditions. (The filaments may be coupled together at their proximal ends in a frustoconical construct, or at their proximal and distal ends in a tubular shape.)

As will be appreciated by those skilled in the art, the braid geometry and material properties are intimately related to the radial force and time constant of the valve. Since the valve is useful in a vessels of arteries of different diameters and flow conditions, each implementation can have a unique optimization. By way of example only, in one embodiment, the element has ten filaments, whereas in another embodiment, the element has forty filaments. Preferably, the filament diameter is chosen in the range of 0.025 mm to 0.127 mm, although other diameters may be utilized. Preferably, the braid angle (i.e., the crossing angle assumed by the filaments in the fully open position—the shape memory position) is chosen in the range of 100° to 150°, although other braid angles may be used. Preferably, the Young's modulus of the filament is at least 100 MPa, and more preferably at least 200 MPa.

The polymer 42' can be coated onto the braid 40' by several methods, including by spraying, spinning, electro-spinning, bonding with an adhesive, thermally fusing, mechanically capturing the braid, melt bonding, dip-coating, or any other desired method, to form a filter. The filter can either be a material with pores such as ePTFE, a solid material that has pores added such as polyurethane with laser drilled holes, or the filter can be a web of very thin filaments that are laid onto the braid.

Where the polymer filter is a web of thin filaments, the characteristic pore size of the filter can be determined by attempting to pass beads of different diameters through the filter and finding which diameter beads are capable of passing through the filter in large quantities. The very thin filaments can be spun onto a rotating mandrel according to U.S. Pat. No. 4,738,740 with the aid of an electrostatic field or in the absence of an electrostatic field or both. The filter thus formed can be adhered to the braid structure with an adhesive or the braid can be placed on the mandrel and the filter spun over it, or under it, or both over and under the braid to essentially capture it. The filter can have some pores formed from spraying or electrospinning and then a secondary step where pores are laser drilled or formed by a secondary operation. In one embodiment a material capable of being electrostatically deposited or spun is used to form a filter on the braid, with the preferred material being capable of bonding to itself. The filter may be made of polyurethane, pellethane, polyolefin, polyester, fluoropolymers, acrylic polymers, acrylates, polycarbonates, or other suitable material. The polymer is spun onto the braid in a wet state, and therefore it is desirable that the polymer be soluble in a solvent. In the preferred embodiment, the filter is formed from polyurethane which is soluble in dimethylacetamide. The polymer material is spun onto the braid in a liquid state, with a preferred concentration of 5-10% solids for an electrostatic spin process and 15-25% solids for a wet spin process.

As another alternative construct for polymer-coating the braid, the braid can be dip-coated to form a filter onto the braid. The braid is mounted on a mandrel having the same outer diameter as the inner diameter of the fully expanded braid. The mandrel is preferably polytetrafluoroethylene (PTFE)-coated steel, in which the PTFE acts as a release surface. Alternatively, a non-coated mandrel may be used. It is important that inner diameter of the braid and the outer diameter of the mandrel not be spaced from each other when the braid is mounted on the mandrel. Thus they preferably have a common diameter within a tolerance of ±0.065 mm. Keeping the entire inner braid in contact with the mandrel allows for the filaments to be evenly coated with the polymer, as subsequently described, so that the filter valve expands uniformly after the polymer dries. Alternately, the braid can be mounted on an oversized mandrel (greater than the inner diameter of the braid), but such will result in an increase in the braid angle of the filaments, and thereby resize the filter valve and effect the expansion force thereof. In an alternate arrangement the braid may be mounted within a tubular mandrel having the same size as the outer diameter of the braid, provided with like tolerances described above. As yet another alternative, the braid can be mounted inside an undersized tubular mandrel (having an inner diameter smaller than the outer diameter of the braid), but such will result in a decrease in the braid angle of the filaments, and thereby also resize the filter valve and effect the expansion force thereof. The type of mandrel (solid or tubular), and the location of the braid thereon (external or internal), will effect localization of the polymer on the braid (providing a smooth internally coated filter valve for external mounting on a solid mandrel and providing a smooth externally coated filter valve for internally mounting within a tubular mandrel), and thereby alter areas of lubricity for the resulting filter valve.

Once the braid is tightly mounted on (or within) the mandrel, the braid is dip coated into a polymer solution at a controlled steady rate. The solution is an elastomeric thermoplastic polymer dissolved in a solvent system with a vapor point ranging from 30-200° C. to produce a solution with a dynamic viscosity range of 50-10,000 cP. The rate of decent and accent is inversely dependent upon the viscosity of the solution and ranges from 1-100 mm/sec. The rate is critical to provide an even coating of the polymer on the braid, to allow wetting of all surfaces of the braid even at locations where the braid filaments are in contact with the mandrel and consequent wicking of the polymer coating into the braid particularly to the surface in contact with the mandrel, and to release air bubbles that may be trapped during the dipping process. By way of example, in one embodiment of the method for dipping into a pellethane solution (pellethane dissolved in the solvents dimethylacetamide (DMA) and tetrahydrofuran (THF)), the rate is such that the dwell time of a 135 mm (6 inch) braid is 16 seconds. The rate is also preferably such that the polymer wicks down the length of the entire braid during withdrawal of the braid from the solution. The braid is dipped one time only into the solution to limit the thickness of the coating and thereby prevent restraint on the braid filaments and/or control smoothness of the polymer coating membrane. The controlled rate may be controlled by coupling the mandrel to a mechanized apparatus that dips and raises the braid on the mandrel at the steady and controlled rate into the polymer solution.

After the braid is withdrawn from the polymer solution, the solvent is evaporated over a time frame relative and temperature range corresponding to the solvent boiling point, with higher temperatures and longer durations utilized for high vapor point solvents. All preferred polymer solutions use some DMA to control the uniformity of the coating thickness, and may use THF to control the rate of solvent evaporation. The ratio of high vapor point solvents such as DMA to low vapor point solvents such as THF allows for control over the rate of transition from a lower viscosity high solvent content polymer solution to a high viscosity low solvent content polymer solution to a solid solvent free material, affecting the quality of the polymer membrane. In one method, the solvents are released in an oven heated to a temperature above the boiling point of DMA (165° C.) in order to rapidly release the DMA. A preferred time of heating at this temperature is 5 minutes which is sufficient to release the DMA. It is appreciated that THF has a substantially lower boiling point (66° C.) and will vaporize quickly without such substantial heating. Alternatively, the polymer-coated braid can be oven heated at a temperature below the boiling point of DMA, e.g., 80° C.-100° C., which will release of the DMA from the coated braid, but at a slower rate than would occur above the boiling point of DMA. This temperature rapidly drives off the DMA while keeping the coating braid safely below the melting or softening point of the braid. A preferred time of heating at this temperature is 10 minutes which is sufficient to release the DMA. As yet another alternative, the polymer-coated braid can be allowed to dry ambient room temperature which results in DMA release occurring at a slower rate than each of the above.

After the solvents have been released from the polymer-coated braid, the coated braid is cooled below the glass transition temperature of the polymer to plasticize the polymer on the braid. Once cooled, the coated braid is released from the mandrel. If the mandrel is coated with PTFE, the braid may self-release from the mandrel or may be readily released. If the mandrel is uncoated, a release agent such as isopropyl alcohol (IPA) may be used to facilitate removal of the coated braid from the mandrel. The resulting elastomeric membrane filter formed on the braid may be elastically deformed over a range of 100-1000% elongation. In addition to pellethane, the membrane may be formed from, but not limited to, other thermoplastic elastomers including other urethanes such as aliphatic polyether-based thermoplastic polyurethanes (TPUs), and styrene-isoprene-butadiene-styrene (SIBS). These polymers may be dissolved in appropriate solvents or heated to their melting point to form a fluid.

By way of example, various embodiments of microvalves suitable for use as a dynamic pressure controlled element 38' are disclosed in co-owned U.S. Pat. No. 8,696,698 and co-owned US Pub. Nos. 20150272716 and 20150306311, which are hereby incorporated by reference herein in their entireties.

A static pressure-control element 38" can be actuated to expand or can be self-expanding. The static element 38" can comprise a fluid inflatable balloon 40" (FIGS. 6 and 7), a self-expanding (non-dynamic) filter 40" (FIG. 8), or a mechanically expandable malecot catheter 40"" (FIG. 9). Each of these static elements 38" can occlude a vessel by being sufficiently expanded to block flow within the vessel around the static pressure-controlled element, and do not modulate in size in view of localized fluid pressure conditions within the vessel and about the element 38". Similarly, the static element 38" can also include radiopaque markers 44" to fluoroscopically identify its location within the vessel.

Referring to FIG. 10, the system may also include an access needle 50 provided with a proximal opening 52, a distal opening 54, a lumen 56 therebetween, and a piercing tip 58. The access needle 50 is preferably curved. The piercing tip 56 may be at the end of a removable obturator 60, which when removed exposes the distal opening 54. The piercing tip 56 is configured and sized to directly pierce a vessel, and particularly the portal vein, and enter into the interior of the portal vein in a manner that communicates the distal opening 54 of the access needle with the interior of the portal vein. In an embodiment, the access needle includes a lumen sized to permit longitudinal passage of the guide sheath 12 therethrough. The system may also include an exchange device (not shown) to facilitate displacement of the access needle 50 over the guide sheath 12, particularly after the guide sheath has been inserted into the portal vein, as described hereinafter.

Referring now to FIG. 17, another embodiment of the system 210 is shown. The system 210 includes a catheter 216 having a pressure control element 238 at its distal end. The system further includes an internal pressure-detecting element 280 and/or an external, pressure-responsive, timing element 282 adapted to permit injection of the infusate based on a localized pressure or a timing event correlated to pressure. The pressure-detecting element 280 can be coupled to the proximal or distal ends of the catheter 216, or provided as other structure for co-delivery with the catheter 216 or separate guidance to a suitable location at which pressure is advantageously sensed. The infusion timing element 282 can be coupled to the system directly or wirelessly. The system 210 is further provided with an outer guide sheath and access needle, as previously described with respect to guide sheath 12 and needle 50. The system 210 may optionally be provided with another catheter having another distal occlusion device, as previously described with respect to catheter 14 and occlusion device 28.

The pressure-detecting element 280 can be a pressure sensor or other system that detects the pressure in the heart or at the target organ. The pressure-detecting element 280 may be coupled at the proximal end of the 216, e.g., at a multi-port hub 284, but is in communication with the distal end of the catheter 216 and identifies to the user the local pressure thereat. The identification may occur with a meter or display 286 coupled to the pressure-detecting element 280. This permits injection of the infusate during an intended blood pressure; change in blood pressure; or at a prescribed time delay relative to a change in pressure at the heart or in the target organ. The pressure-detecting element 280 can, e.g., permit or activate infusion during the diastolic period and halt or deactivate infusion during the systolic period; this increases the pressure differential in the target organ and maximizes organ uptake of the infusate.

Additionally, the pressure-detecting element 280 may be optionally coupled to a pump 288 that automatically injects the treatment agent through the multi-port hub 284 upon detection of the pressure condition. As the pressure events may cycle quickly, automation of the infusion upon the detected pressure condition removes the human response time as a limitation in rapidly responding to the detected pressure condition. Moreover, the pump 288 can be operated to modify the rate of infusion in a closed loop fashion to produce an intended pressure value during administration of the therapy.

In an embodiment, the pressure-responsive, infusion timing element 282 is adapted to permit injection of the infusate via the pump 288 at a set time offset following a portion of the cycle of the heart rate, with such delay capable of accounting for a consequent change in pressure occurring in the target organ after a pressure change at the heart. By way of example, the timing element may include a connection to an EKG or a pulse-oximeter.

Figure 12:
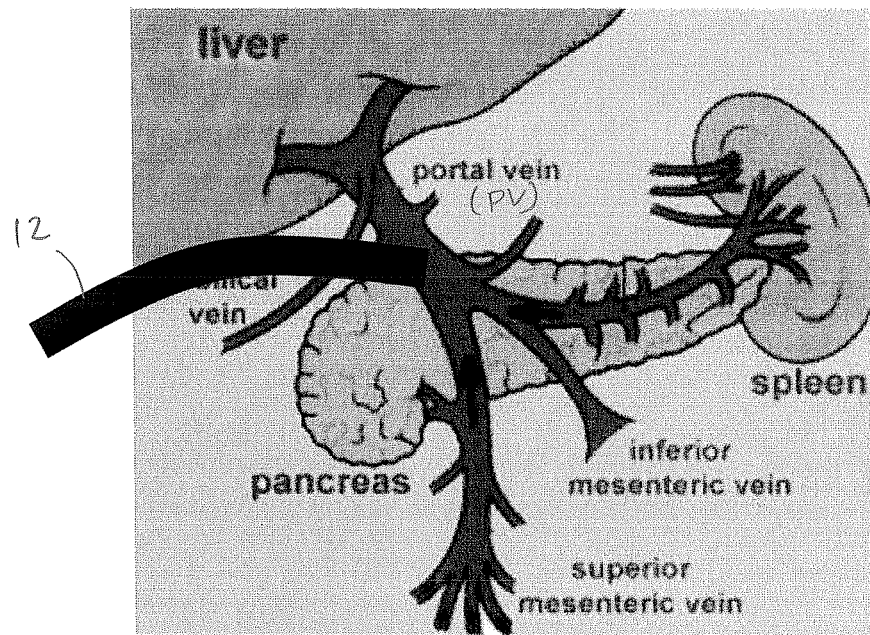

Turning now to FIG. 11, in one method of use described with respect to system 10 (but generally applicable to systems 110 and 210), the access needle 50 is deployed into a primary vessel from which feeder vessels extend or into a vessel adjacent and directly communicating with the primary vessel. By way of example, for treatment of feeder vessels extending from the splenic vein (SV), the access needle 50 is inserted directly into the adjacent portal vein (PV), preferably without traversing other endovascular vessels, which can be achieved by directly puncturing the portal vein with the aid of ultrasound visualization. Then, as shown in FIG. 12, the guide sheath is inserted through the access needle and into the portal vein, and the access needle is withdrawn, leaving the guide sheath in position within the portal vein (PV). Alternatively, the exchange device (not shown) is used to replace the access needle with the guide sheath. Regardless, the guide sheath 12 may be advanced into the portal vein (PV). The first and/or second catheters 14, 16 may be preloaded in the guide sheath 12 and preferably advanced toward the distal end 22 of the guide sheath (as shown in FIG. 2). Alternatively, the guide sheath 12 may be advanced empty of the first and/or second catheters 14, 16, with such catheters advanced together thereafter or individually as necessary. As yet another alternative, the guide sheath 12 may be advanced with the first and/or second catheters 14, 16 partially advanced within the guide sheath. In accord with alternate methods using both first and second catheters 14, 16, the first catheter 14 is advanced to the distal end of the guide sheath after the guide sheath is situated in the portal vein (PV).

Figure 13:
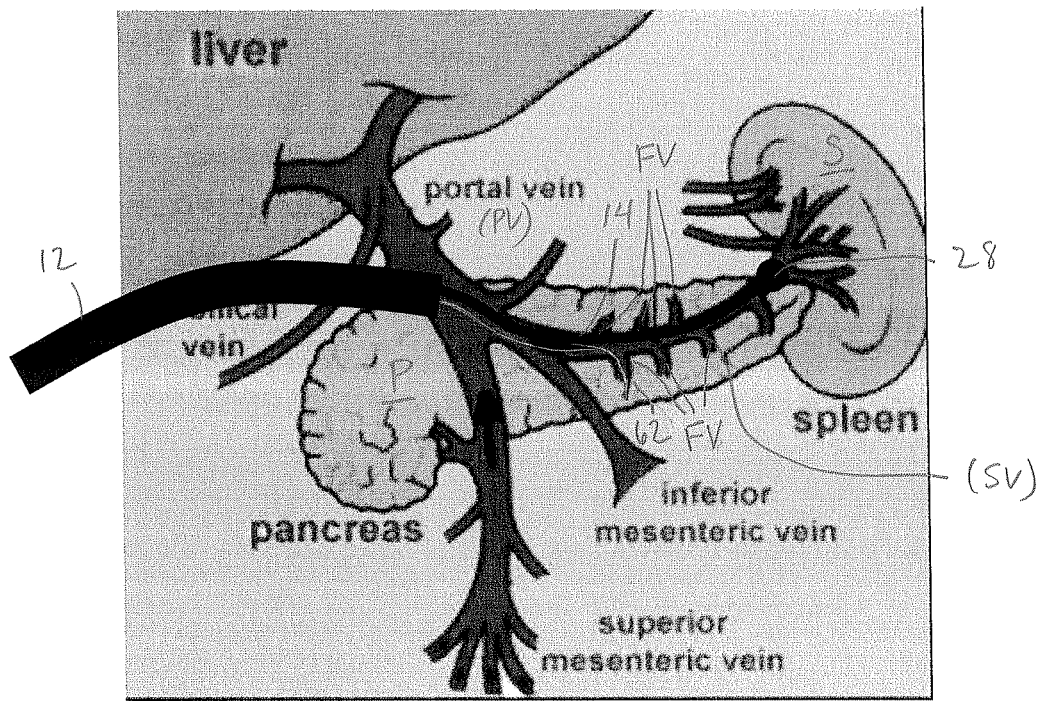

Referring to FIG. 13, in accord with one method, the first occlusion element 28 at the distal end of the first catheter 14 is then advanced out of the guide catheter 12, through the portal vein (PV) and into the splenic vein (SV) traversing the pancreas (P) and to the origin of the spleen (S). Once the first occlusion element 28 is at the end of the splenic vein (SV) adjacent the spleen (S), the first occlusion device 28 is expanded, e.g., via fluid inflation along the first catheter 14, to occlude portal venous flow into the spleen.

A large bolus of contrast agent is then injected into the portal vein (PV) and through the splenic vein (SV) to image the portal and splenic vein anatomy. Preferably, the contrast agent is injected through the guide catheter 12 (either through lumen 18 shown in FIG. 3 and around the first and second catheters, or within a dedicated lumen thereof); less preferably, the contrast agent may be injected through holes in the first catheter located proximal of the first occlusion element, however, the volume and pressure will not be as preferable as injection through the larger diameter guide catheter. The contrast agent is prevented from entering the spleen (S) by the first occlusion element 28, and therefore is targeted to the splenic vein (SV) and feeder vessels (FV) extending off of the splenic vein (SV) and deep into the pancreas (P). The first occlusion element 28 may then remain in the expanded state, or optionally is contracted via deflation to again permit blood flow between the spleen (S) and the portal vein (PV).

A guidewire 62 is then advanced through the guide catheter 12, under guidance of the visualization provided by the contrast agent, and guided into a first feeder vessel extending from the splenic vein. The guidewire 62 is a microwire, preferably 0.014-0.020 inch. Using the first embodiment of the treatment system 10, the guidewire is advanced parallel and non-coaxial to the first catheter; using the second embodiment of the treatment system 110, the guidewire is advanced through the first catheter and out of its side opening 174 (FIG. 16).

Figure 14:
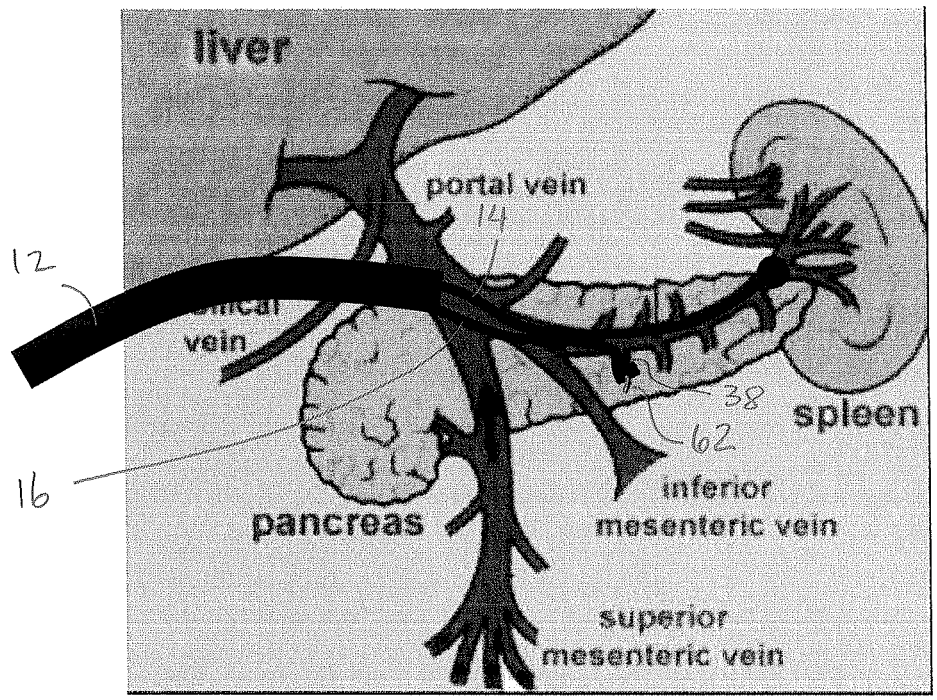

Turning to FIG. 14, the second catheter 16 is then advanced over the guidewire 62 so that the second occlusion device 38 is at or beyond the ostium of the first feeder vessel. If the second occlusion device is a static device 38", 38"', 38"", it is then expanded to block fluid passage within the first feeder vessel. If the second occlusion device 38' is dynamic, no pre-expansion to the feeder vessel wall is required, as the second occlusion device will automatically expand thereto when subject to the increased fluid pressure of the injected treatment agent. The treatment agent is then injected under pressure through the second catheter 16, distally of the second occlusion device 38, and into the feeder vessel. The treatment agent is preferably injected in combination with a contrast agent to monitor the progress of tissue penetration.

Depending on the type of treatment agent, different infusion procedures are preferably utilized. For a 'heavy' infusate, such as radioembolization spheres, the agent is infused from outside the body through the second catheter 16 at a relatively high pressure, e.g., 300-1200 psi, in order to drive the spheres forward within the second catheter 16 and vessels as fast as possible so that the spheres do not settle out of suspension and deliver before reaching the target tissue, i.e., tumor. The infusion pressure preferably generates a net increase in fluid pressure within the vessel of 10 mmHg to 200 mmHg above systemic pressure. A 'heavy' infusate would substantially reflux if infused through a traditional microcatheter. The second catheter 16 and second occlusion element 38 are capable of supporting rapid increases in pressure, on the order of milliseconds, which is required in such procedures. Such an infusion procedure may result in the development of high shear rate conditions, which is not an issue for a 'heavy' infusate.

For various biologic infusates, particularly cells such as CAR-T, CAR-NK, TCR-R, TCR-NK, and β-cells or combinations thereof, relatively lower shear rates are desired to prevent damage to the cells and/or to prevent premature activation of the cells. Therefore, a different method is preferred. The cells are infused from outside the patient through the second catheter 16 at a relatively low pressure, e.g., below 300 psi, and after the cells are out of the second catheter and into the feeder vessel, where there is a lower shear rate, a bolus of saline is flushed through the second catheter at a significantly higher pressure (above 300 psi) to promote distal flow of the biologic infusate deep into the tumor and support forward flow of the infusate from the feeder vessel into newly opened regions of the tumor and/or tissue. The two steps of infusing the biologic and then flushing can be repeated.

Referring back to FIG. 6, in one embodiment for biologic infusion, the proximal end of the second catheter 16 includes a hub 90 coupled to first and second ports 92, 94 at a two-way stopcock 96. The first port 92 is intended to receive the biologic infusate, and the second port 94 is intended to receive the saline. The stopcock 96 is first set to communicate the first port 92 with the second catheter 16, and the biologic infusate is infused at relatively low pressure. The stopcock 96 is then reconfigured to communicate the second port 94 with the second catheter 16, and the second catheter is flushed in accord with a desirable pressure and time profile. For example, the second catheter 16 may be flushed at a relatively low pressure with 2 mL to clear remaining biologic infusate from the second catheter, and then flushed with 20 mL at a relatively higher pressure of 1200 psi; or may be cycled up and down between 300 to 2000 psi; other suitable profiles for infusing the biologic infusate and the saline flush at relatively different pressures can be used. The infusion of the biologic infusate followed by saline is preferably repeated to promote deep penetration of the biologic infusate into the tissues. The infusion and flush through the second catheter may be effected manually or via a pump.

Optionally, the infusion pressure can be measured after each infusion in order to monitor the infusion pressure relative to systemic pressure. More particularly, a standard sphygmomanometer or other blood pressure monitor can be used measure systemic patient blood pressure. Then, a blood pressure monitor coupled to the hub of the second catheter is utilized to measure pressure at the infusion target. The treatment agent is infused until the infusion target measures systemic pressure, 10 mmHg above systemic pressure, or 200 mmHg above systemic pressure.

Figure 18:
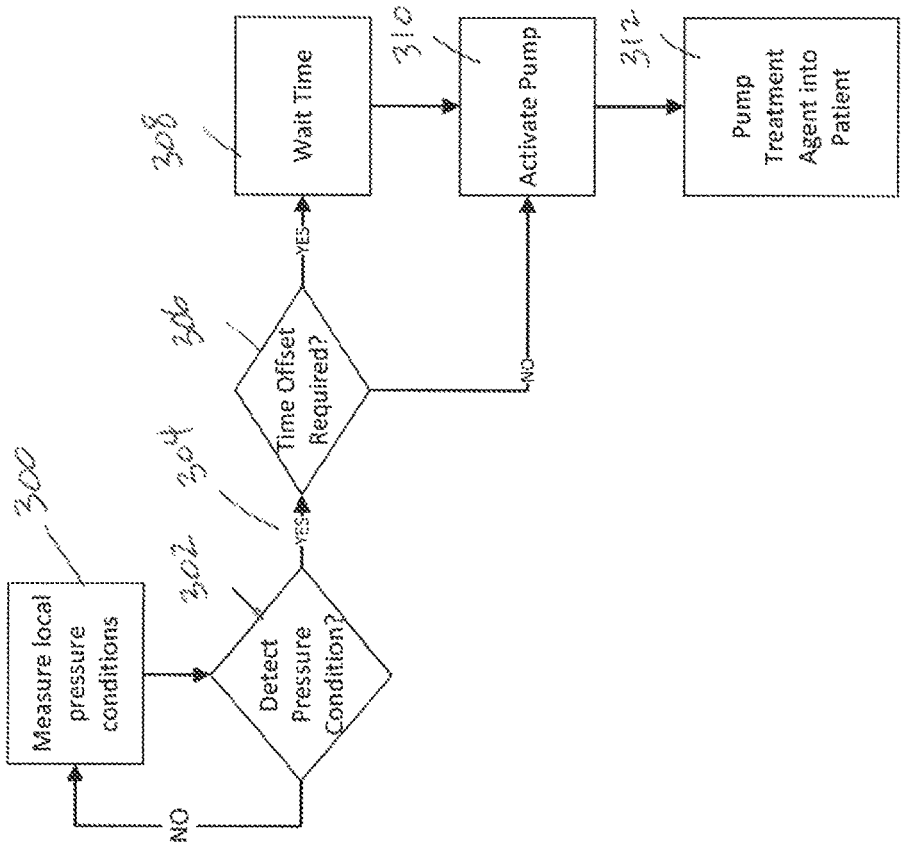
FIG. 18 is a flow chart of a method of using a system described herein.

Referring now to FIG. 18, in accord with another method for infusion of a treatment agent, a system may be provided in accord with system 210 of FIG. 17 and advanced into the patient. The system 210 can include both internal, pressure-detecting element 280 and external, pressure-responsive, timing element 282, or the pressure-detecting element without the timing element. At an appropriate point in the procedure, the pressure-detecting element 280 is operated at 300 to detect a pressure condition at the target location for infusion or another local condition within the patient, e.g., at the heart. The system continually monitors for such condition at 302 until such condition occurs at 304. Upon detection of the pressure condition at 304, the system determines at 306 whether a time offset has been set to delay injection of the treatment agent for a preset period of time after detection of the pressure event. If a time offset has been set at 306, the system waits the time offset at 308. Then, after the delay at 308, the pump is activated at 310 to infuse at 312 a determined amount of treatment agent into the patient. If no offset has been set at 306, the system immediately activates the pump at 310. The method includes infusing a full dose of the treatment agent at 312, or alternatively infusing a partial dose of the treatment agent. A defined portion of the dose can be infused during each of several pressure conditions being met. For example, for a treatment dose of 100 mL, four partial doses each of 25 mL may be infused, each upon the detection of the preset pressure condition.

Figure 19:
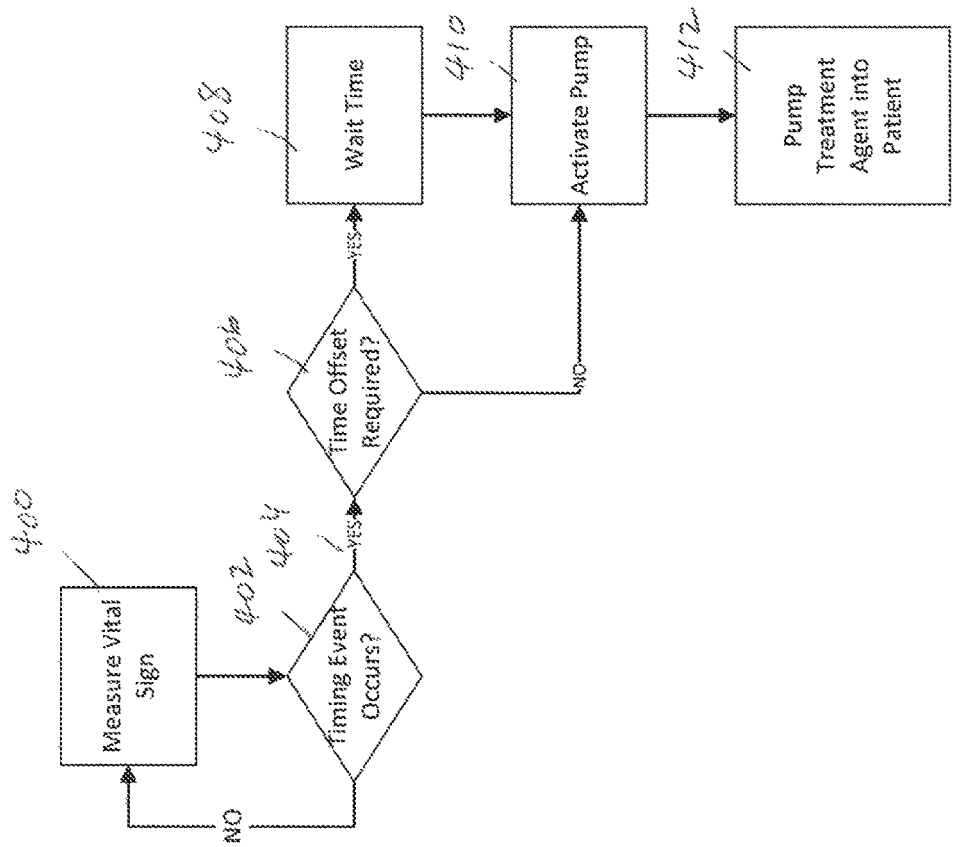
FIG. 19 is another flow chart of a method of using a system described herein.

Referring now to FIG. 19, in accord with another pressure-responsive method for infusion of a treatment agent, a system may be provided in accord with system 210 of FIG. 17 and advanced into the patient. The system can include both intravascular pressure-detecting element 280 and timing element 282, or the timing element 282 without intravascular pressure-detecting element. At an appropriate point in the procedure, the timing element 282 is operated 300 to measure vital signs of the patient. Such vital signs may be measured externally of the patient and does not require direct monitoring of pressure within the patient's system. However, the vital sign measured is correlated to the patient's pulse and thus reliably indicates pressure events occurring within the vascular system of the patient. By way of example, a pulse oximeter or an EKG can be used as the timing element. The system continually monitors for a timing condition at 402 until a suitable timing condition is detected at 404. Upon detection of the timing event at 404, the system determines at 406 whether a time offset has been set to delay injection of the treatment agent for a preset period of time after detection of the timing event. If a time offset has been set at 406, the system waits the time offset at 408. Then, after the delay at 408, the pump is activated at 410 to infuse at 412 a determined amount of treatment agent into the patient. If no offset has been set at 406, the system immediately activates the pump at 310. The method includes infusing a full dose of the treatment agent at 412, or alternatively infusing a partial dose of the treatment agent. It is appreciated that even though the system measures vital signs external of the vascular system, it is adapted to pressure-responsive to the intravascular pressure.

The methods described with respect to FIGS. 18 and 19 can be used separately or can be combined where both a pressure-detecting element and a timing element are incorporated into the system.

Regardless of the method, infusion preferably continues until either the target dose is infused, enhancement of downstream non-target collateral vessels is realized through visualization, or a target pressure is reached.

At the conclusion of infusion through the second catheter 16 within the feeder vessel, the second occlusion element 38, 138 is collapsed (or, in accord with alternate embodiments, the only occlusion element 238 is collapsed). As an option, while the second occlusion element 38, 138, 238 is deployed within the feeder vessel and before it is collapsed, the vessel is slowly aspirated to relieve pressure and prevent backflow of infusate. Once the second occlusion element is collapsed, the treatment agent may begin to travel through the splenic vein and enter the portal vein. Therefore, saline is again further infused through at least one of the second catheter and the guide catheter to dilute the treatment agent as the treatment agent begins systemic circulation.

Figure 15:
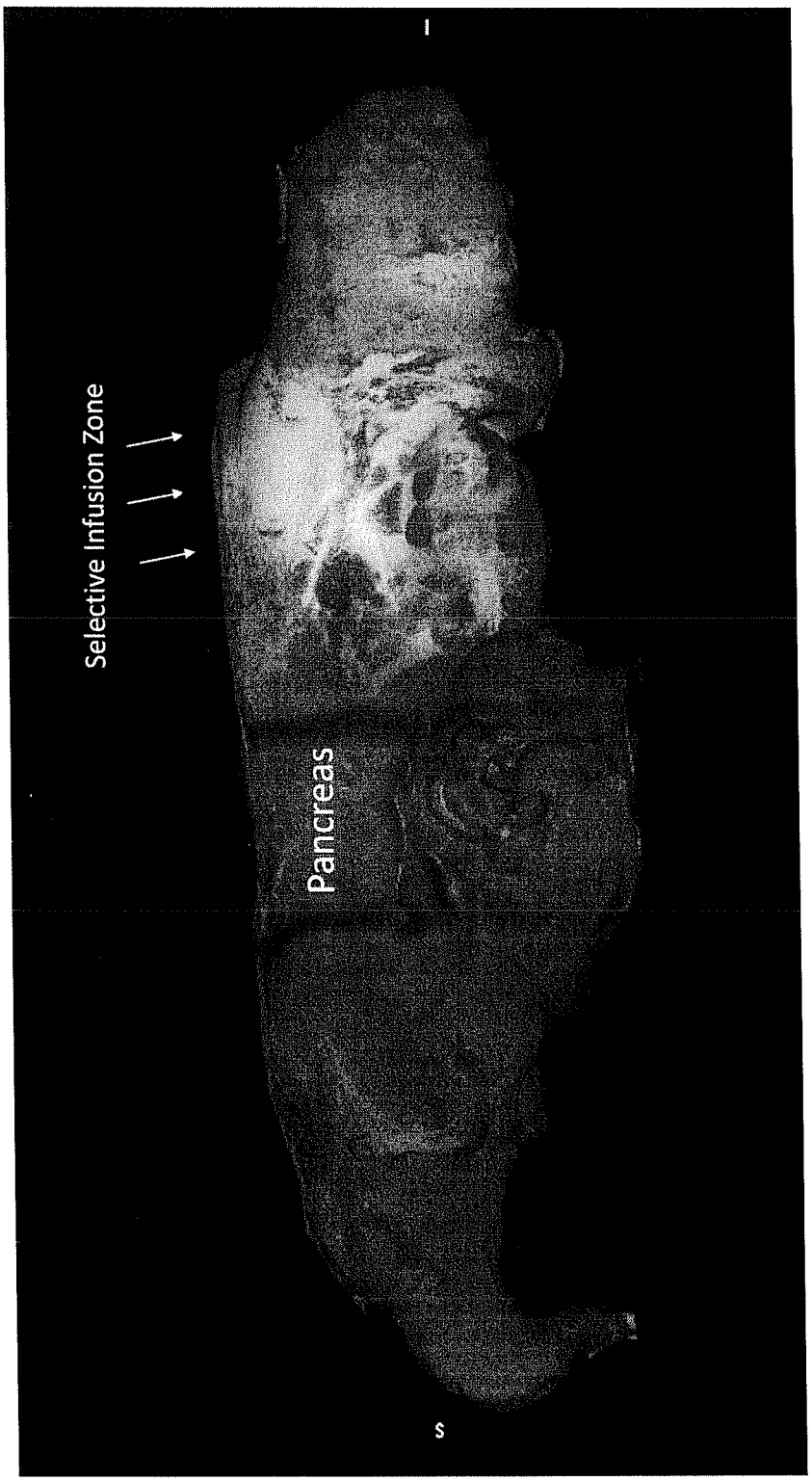
FIG. 15 is a photograph showing exemplar results of treatment by pressure-controlled therapeutic delivery on a porcine pancreas.

The treatment may then be continued by advancing the guidewire 62 into a different second feeder vessel, the second catheter over the guidewire into the second feeder vessel and providing an additional portion of the dose of the treatment agent under pressure into the second feeder vessel. The process may be repeated until an appropriate dose has been infused to selected target tissue through the one or more of the feeder vessels. After the infusion is completed, the first and second catheters and guide catheter are then withdrawn from the portal vein and out of the patient. Turning to FIG. 15, a porcine pancreas infused in accord with the described methods is shown, with the highlighted area illustrating the depth of penetration obtained by the infusate using methods described herein.

The system, as indicated above, can be used without the first catheter 14 and first occlusion element 28; infusion is effected through the second catheter alone. The pressure-detecting element and/or infusion timing elements are consequently coupled to the second catheter.

The system and procedures described herein provide several advantages over known prior art. Relative to a system including two coaxial balloons (or two filters), the treatment system and methods herein provide precise, targeted infusion of the treatment agent. In addition, the treatment system and method allow high-pressure infusion permitting the treatment agent to extend deeper into target tissues and even open up vessels that may be otherwise closed to treatment. This is, at least in part, because infusion is presented at the end of the system and because the system as used in the method permits pressure control. It should be understood that it is not feasible to generate significant pressure to overcome tumor pressure in large cross-sectional vessels, such as the portal or splenic veins in view of the size of the catheter used in prior devices. In order to achieve significant injection pressures measured at the hub of the second catheter, a preferred and suitable ratio of catheter inner diameter to vessel diameter is 1:8; i.e., a 0.021 inch inner diameter catheter is well suited for 0.168 inch vessel. In addition, the dynamic second occlusion element 38" automatically dilates as the pressure increases; this permits, e.g., up to a three times an increase in diameter relative to an initial diameter automatically in response to local pressure conditions resulting from the infusion of the treatment agent. Moreover, the dynamic second occlusion element 38" is both a filter and a valve. The filter allows flow of plasma and contrast agent to provide an indication of the local flow conditions to the interventionalist. The valve dynamically expands substantially immediately during deployment to trap reverse flowing blood and rapidly reaches arterial systemic mean pressure. The valve operates to occlude the feeder vessel, and as pressure increases and the vessel seeks to expand, the valve increases occlusion. In distinction, a balloon becomes less occlusive as the pressure increases and the vessel expands.

There have been described and illustrated herein embodiments of a treatment system and methods of pressure-controlled therapeutic delivery. While particular embodiments of the invention have been described, it is not intended that the invention be limited thereto, as it is intended that the invention be as broad in scope as the art will allow and that the specification be read likewise. Thus, while particular embodiments include preferred dimensions for the occlusion elements in relation to particular vessels in around the pancreas, it will be appreciated that the system can be adapted for a treatment provided through vessels in and around other organs, and the occlusion elements can be likewise adapted for extending completely across the relevant vessels of such other organs. Also, while the system is primarily adapted for therapeutic treatment of humans, it has been demonstrated on the porcine tissues and organs, and can be used for the treatment of mammals, in general. Further, while the systems has been described for particular treatment via the portal vein, the system and the pressure-responsive methods of use, may also be used to infuse treatment agents during arterial side infusions. Moreover, while various exemplar therapeutics have been disclosed, the system and methods are not limited to any specific therapeutic agent. By way of further example, and not by limitation, checkpoint inhibitors and oncolytic virus can also be used as the therapeutic agent. Also, combinations of therapeutic agents may be infused. While particular dimensions and ratios have been disclosed, it will be understood that the invention is not limited thereto. It will therefore be appreciated by those skilled in the art that yet other modifications could be made to the provided invention without deviating from its scope as claimed.

What is claimed is:

1. A method for delivering of a therapeutic agent under pressure to a target organ having a tumor, the target organ in communication with one or more feeder vessels extending from a relatively larger primary vessel, the primary vessel and feeder vessels having a systemic pressure, the method comprising:
    a) providing a catheter having a proximal end, a distal end, a lumen extending between the proximal and distal ends and having a distal orifice, and an occlusion element located at the distal end, proximal of the orifice, the occlusion element having an expanded configuration adapted to extend across the feeder vessels;
    b) advancing a guide sheath into or adjacent the primary vessel;
    c) advancing the occlusion element out of the guide sheath and into one of the feeder vessels;
    d) injecting a therapeutic agent through the catheter at a first pressure to cause the therapeutic agent to flow through the feeder vessels at a pressure higher than the systemic pressure; and
    e) injecting a bolus of saline through the catheter at a second pressure relatively higher pressure than the first pressure to cause the therapeutic agent to flow through the feeder vessels and penetrate into the tumor of the target organ.

2. The method according to claim 1, wherein:
the first pressure is below 300 psi, and the second pressure is at or above 300 psi.

3. The method according to claim 1, wherein:
the first pressure is 300 to 1200 psi.

4. The method according to claim 1, wherein:
the pressure of the injected therapeutic agent generates a net increase in fluid pressure in the feeder vessels of 10 mmHg to 200 mmHg above systemic pressure.

5. The method according to claim 1, wherein:
the occlusion element is dynamic such that the occlusion element automatically expands to the expanded configuration and contracts to a contracted configuration in response to fluid pressure on proximal and distal sides of the occlusion element, wherein in the contracted configuration the occlusion element is not adapted to extend across the feeder vessels.

6. The method according to claim 1, further comprising:
before advancing the guide sheath, piercing a hole in the primary vessel or a vessel adjacent and directly communicating with the primary vessel with an access needle.

7. The method according to claim 1, wherein:
the primary vessel is a vein.

8. The method according to claim 1, wherein:
the therapeutic agent comprises one of a radio-embolization agent and a biologic agent.

9. The method according to claim 1, wherein:
the therapeutic agent is a biologic agent selected from a group consisting of one of CAR-T cells, CAR-NK cells, TCR-R cells, TCR-NK cells, β-cells, and a combination of two or more of the cells.

10. The method according to claim 1, wherein:
the therapeutic agent includes one or more of a biologic cell, a checkpoint inhibitor, and an oncolytic virus.

11. The method according to claim 1, wherein:
the guide sheath is advanced into a portal vein, the catheter is advanced into a splenic vein.

12. A method for delivering of a therapeutic agent under pressure to a target organ having a tumor, the target organ in communication with a vein, the vein having a systemic pressure, the method comprising:
    a) providing a catheter having a proximal end, a distal end, a lumen extending between the proximal and distal ends and having a distal orifice, and an occlusion element located at the distal end, proximal of the orifice, the occlusion element having an expanded configuration adapted to extend across the vein;
    b) advancing a guide sheath into or adjacent the vein;
    c) advancing the occlusion element out of the guide sheath and into the vein;
    d) injecting an immunotherapy agent through the catheter and out of the orifice at a first pressure to cause the immunotherapy agent to flow into the vein; and
    e) injecting a bolus of a fluidic agent different from the immunotherapy agent through the catheter and out of the orifice at a second pressure relatively higher pressure than the first pressure to force the immunotherapy agent through the vein and penetrate into the tumor of the target organ.

13. The method of claim 12, wherein the vein is the splenic vein.

14. The method of claim 12, wherein after advancing the occlusion element out of the guide sheath, the occlusion element is opened into the expanded configuration.

15. The method of claim 12, wherein the immunotherapy agent is selected from a group consisting of one of CAR-T cells, CAR-NK cells, TCR-R cells, TCR-NK cells, β-cells, and a combination of two or more of the cells.

16. The method of claim 12, wherein the fluidic agent is saline.

17. The method of claim 12, wherein the target organ is a pancreas.

18. The method of claim 17, wherein the vein is a splenic vein.

19. The method of claim 17, wherein the vein is a portal vein.

20. The method of claim 12, wherein the first pressure is below 300 psi, and the second pressure is above 300 psi.

21. The method of claim 1, wherein the target organ is a pancreas.

22. The method of claim 1, wherein the target organ is a liver.

* * * * *